(12) United States Patent
Wilson et al.

(10) Patent No.: US 10,696,985 B1
(45) Date of Patent: Jun. 30, 2020

(54) REVERSIBLY CROSSLINKED ENDOSOMOLYTIC POLYMER VESICLES FOR CYTOSOLIC DRUG DELIVERY

(71) Applicant: Vanderbilt University, Nashville, TN (US)

(72) Inventors: John T. Wilson, Nashville, TN (US); Daniel Shae, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/615,753

(22) Filed: Jun. 6, 2017

Related U.S. Application Data

(60) Provisional application No. 62/346,428, filed on Jun. 6, 2016.

(51) Int. Cl.

| | |
|---|---|
| C08F 293/00 | (2006.01) |
| C08G 85/00 | (2006.01) |
| A61K 47/32 | (2006.01) |
| C12N 15/88 | (2006.01) |
| C12N 15/11 | (2006.01) |
| C12N 15/87 | (2006.01) |
| A61K 39/395 | (2006.01) |
| A61K 39/00 | (2006.01) |
| A61K 48/00 | (2006.01) |
| C12N 15/09 | (2006.01) |

(52) U.S. Cl.
CPC .......... *C12N 15/88* (2013.01); *A61K 39/0005* (2013.01); *A61K 39/0012* (2013.01); *A61K 39/39558* (2013.01); *A61K 48/00* (2013.01); *C12N 15/11* (2013.01); *C12N 15/87* (2013.01); *A61K 39/00* (2013.01); *C12N 15/09* (2013.01)

(58) Field of Classification Search
None
See application file for complete search history.

(56) References Cited

U.S. PATENT DOCUMENTS

| | | | |
|---|---|---|---|
| 7,592,326 | B2 | 9/2009 | Karaolis |
| 7,709,458 | B2 | 5/2010 | Karaolis et al. |
| 8,450,293 | B2 | 5/2013 | Jones et al. |
| 9,315,523 | B2 | 4/2016 | Jones et al. |
| 9,549,944 | B2 | 1/2017 | Dubensky et al. |
| 9,597,391 | B2 | 3/2017 | Ebensen et al. |
| 10,081,658 | B2 * | 9/2018 | Kalyanaraman ....... A61K 39/21 |

FOREIGN PATENT DOCUMENTS

| | | |
|---|---|---|
| WO | WO 2011/003025 A1 | 1/2011 |
| WO | WO 2014/093936 A1 | 6/2014 |
| WO | WO 2014/099824 A1 | 6/2014 |
| WO | WO 2014/179335 A1 | 11/2014 |
| WO | WO 2014/179760 A1 | 11/2014 |
| WO | WO 2014/189805 A1 | 11/2014 |
| WO | WO 2015/074145 A1 | 5/2015 |
| WO | WO 2016/096174 A1 | 6/2016 |
| WO | WO 2016/096577 A1 | 6/2016 |
| WO | WO 2016/120305 A1 | 8/2016 |
| WO | WO 2016/145102 A1 | 9/2016 |
| WO | WO 2017/027645 A1 | 2/2017 |
| WO | WO 2017/027646 A1 | 2/2017 |
| WO | WO 2017/075477 A1 | 5/2017 |

OTHER PUBLICATIONS

Hanson, et al. (Feb. 11, 2015) "Liposomal vaccines incorporating molecular adjuvants and intrastructural T-cell help promote the immunogenicity of HIV membrane-proximal external region peptides", Vaccine, 33(7): 861-68. (Year: 2015).*
Shae, et al. (2019) "Endosomolytic Polymersomes Increase the Activity of Cyclic Dinucleotide STING Agonists to Enhance Cancer Immunotherapy", Nature Nanotechnology, 14(3): 269-78. (Year: 2019).*
IUPAC-IUB Commission on Biochemical Nomenclature Symbols for Amino-Acid Derivatives and Peptides Recommendations (1971); Biochemistry, vol. 11, No. 9, 1972; pp. 1726-1732.
Heller, et al., Combining reactive triblock copolymers with functional cross-linkers: A versatile pathway to disulfide stabilized-polyplex libraries and their application as pDNA vaccines, Journal of Controlled Release 258 (2017) 146-160.
Wilson, et al., Enhancement of MHC-I Antigen Presentation via Architectural Control of pH-Responsive, Endosomolytic Polymer Nanoparticles, The AAPS Journal, vol. 17, No. 2, Mar. 2015 (# 2014), pp. 358-.

(Continued)

*Primary Examiner* — Robert M Kelly
(74) *Attorney, Agent, or Firm* — Stites & Harbison PLLC; Sean P. Ritchie

(57) ABSTRACT

A diblock copolymer, polymer vesicle, and method of forming a polymer vesicle are provided. The diblock polymer includes a hydrophilic first block and a second block including amine containing monomers and hydrophobic monomers. The polymer vesicle includes a diblock copolymer with a hydrophilic first block and a second block including amine containing monomers and hydrophobic monomers, and at least one active agent loaded in the polymer vesicle. The second block forms an inner hydrophobic domain of a vesicle membrane and the hydrophilic block forms a corona facing the exterior and aqueous interior of the vesicle membrane, the corona providing an outer shell that stabilizes the vesicle in aqueous media. The method of forming the polymer vesicle includes synthesizing the diblock copolymer through a polymerization technique selected from the group consisting of addition polymerization, condensation polymerization, and a combination thereof, providing at least one active agent, and assembling the polymer vesicle, the diblock copolymer including a hydrophilic first block and a second block with amine containing monomers and hydrophobic monomers.

43 Claims, 18 Drawing Sheets

(56) References Cited

OTHER PUBLICATIONS

Lane, et al., Dynamic intracellular delivery of antibiotics via pH-responsive polymersomes, Polym. Chem., 2015, 6, 1255-1266.
Zhang, et al., pH and Reduction Dual-Bioresponsive Polymersomes for Efficient Intracellular Protein Delivery, Langmuir 2012, 28, 2056-2065.

* cited by examiner

| Compound | Encapsulation Efficiency (%) | N |
|---|---|---|
| 2'3'-cGAMP | 38+/-3 | >10 |
| c-di-GMP | 26+/-1 | 2 |
| 2'3'-cGAM(PS)$_2$ (Rp/Sp) | 19 | 1 |
| c-[2'FdGMP]-[2'FdAMP] | 76 | 1 |
| ovalbumin | 27 +/- 2 | 3 |
| CpG ODN 1826 | 25 | 1 |
| 5'-ppp-dsRNA | 25 | 1 |
| Pam$_3$CSK4 | 82 | 1 |
| Dextran | 29 | 1 |
| Peptide (QLESIINFEKL) | 68+/-3 | 2 |

FIG. 5

| PEG $M_n$ (kDa) | 2nd block $M_n$ (kDa) | f (%) | Morphology |
|---|---|---|---|
| 2 | 5 | 29 | V |
| 2 | 7.8 | 20 | A |
| 2 | 10.8 | 16 | A |
| 2 | 20 | 9 | A |
| 5 | 9.2 | 35 | C |
| 5 | 14 | 26 | C/S |
| 10 | 20 | 30 | S |

REVERSIBLY CROSSLINKED ENDOSOMOLYTIC POLYMER VESICLES FOR CYTOSOLIC DRUG DELIVERY

RELATED APPLICATIONS

This application claims the benefit of U.S. Provisional Application Ser. No. 62/346,428, filed Jun. 6, 2016, the entire disclosure of which is incorporated herein by this reference.

TECHNICAL FIELD

The presently-disclosed subject matter generally relates to compositions and methods for cytosolic drug delivery. More specifically, the presently-disclosed subject matter relates to methods of forming reversibly crosslinked endosomolytic polymer vesicles and the use thereof for cytosolic drug delivery.

BACKGROUND

Cyclic dinucleotides (CDNs) are ubiquitous small molecule second messengers that regulate a diverse set of processes. Recently, it has been shown that CDNs may have potential applications as therapeutics and/or vaccine adjuvants. For example, certain CDNs have been shown to act as agonists for stimulator of interferon genes (STING), which may inhibit tumor growth and/or boost host antitumor immune response.

However, despite significant research, there remain various challenges which prevent the effective use of CDNs as therapeutics and/or adjuvants. One such challenge includes efficient delivery of CDNs. In particular, poor CDN localization in the cytosolic compartments of tumor associated cells presents a significant barrier to the potential of CDN based cancer immunotherapy.

Accordingly, there remains a need for compositions and methods that provide improved cytosolic drug delivery.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a diblock copolymer comprising a hydrophilic first block and a second block including amine containing monomers, hydrophobic monomers, and optionally crosslinkable monomers. In one embodiment, the hydrophilic block is between about 25% and about 35% of the total mass of the diblock copolymer. In another embodiment, the hydrophilic block is selected from the group consisting of polyethers, polyesters, polycarbonates, polyvinyls, polyamino acids, polysulfobetaines, carboxybetaines, and combinations thereof. In a further embodiment, the hydrophilic block is polyethylene glycol (PEG). In some embodiments, the hydrophilic block has a molecular weight of between about 1 kDa and about 3 kDa.

In some embodiments, a mole percent of the amine containing monomers in the second block is between 40% and 70%. In some embodiments, a mole percent of the hydrophobic monomers in the second block is between 30% and 60%. In some embodiments, a mole percent of the crosslinkable monomers in the second block is between 2% and 16%. In one embodiment, the amine containing monomers are selected from the group consisting of (2-diethylamino) ethyl methacrylate (DEAEMA), 2-(dimethylamino) ethyl methacrylate, 2-(diisopropylamino)ethyl methacrylate, 2-N-morpholinoethyl methacrylate, 2-amino methacrylate hydrochloride, and combinations thereof. In one embodiment, the hydrophobic monomers are selected from the group consisting of acrylates, alkyl methacrylates, methacrylates with fluorinated or aromatic pendant groups, and combinations thereof. In another embodiment, the alkyl methacrylates are selected from the group consisting of butyl methacrylate (BMA), hexyl methacrylate, octyl methacrylate, decyl methacrylate, and/or lauryl methacrylate. In one embodiment, the crosslinkable monomers are selected from the group consisting of pyridyl disulfide monomers, azide-functionalized monomers, thiol-functionalized monomers, amine-functionalized monomers, photocrosslinkable monomers, and combinations thereof. In one embodiment, the terpolymer block has a molecular weight of between 3 kDa and 6 kDa.

In some embodiments, the diblock copolymer includes the formula [polyethylene glycol]$_m$b-[((2-diethylamino)ethyl methacrylate)$_x$-c-(butyl methacrylate)$_y$-c-(pyridyl disulfide ethyl methacrylate)$_z$]$_n$, where m is between 1 and 3 kDa, n is between 3 and 6 kDa, x is between 40 and 70 mole percent, y is between 30 and 60 mole percent, and z is between 0 and 16 mole percent. In one embodiment, m is 2 kDa and n is 4.5 kDa. In one embodiment, x is 57 mole percent, y is 35 mole percent, and z is 8 mole percent. In some embodiments, the copolymer is crosslinked. In some embodiments, the copolymer is self-assembling.

Also provided, in some embodiments, is a polymer vesicle comprising a diblock copolymer including a hydrophilic first block and a second block including amine containing monomers, hydrophobic monomers, and optionally crosslinkable monomers, and at least one active agent loaded in the polymer vesicle. The second block forms an inner hydrophobic domain of a vesicle membrane and the hydrophilic block forms a corona facing the exterior and aqueous interior of the vesicle membrane, the corona providing an outer shell that stabilizes the vesicle in aqueous media. In one embodiment, the diblock copolymer comprises the formula [polyethylene glycol]$_m$b-[(2-diethylamino) ethyl methacrylate)$_x$-c-(butyl methacrylate)$_y$-c-(pyridyl disulfide ethyl methacrylate)$_z$]$_n$, where m is between 1 and 3 kDa, n is between 3 and 6 kDa, x is between 40 and 70 mole percent, y is between 30 and 60 mole percent, and z is between 0 and 16 mole percent. In another embodiment, m is 2 kDa and n is 4.5 kDa. In a further embodiment, x is 57 mole percent, y is 35 mole percent, and z is 8 mole percent. In some embodiments, the vesicle is pH-responsive. In some embodiments, the vesicle is stable at physiological pH, and is disassembled at a pH of about 6.5. In some embodiments, the vesicle is crosslinked. In some embodiments, the active agent is a stimulator of interferon genes (STING) agonist or antagonist, or a cyclic dinucleotide (CDN). In one embodiment, the STING agonist is released by the vesicle at a pH of about 6.5.

Further provided, in some embodiments, is a method of forming a polymer vesicle, the method comprising synthesizing a diblock copolymer through a polymerization technique selected from the group consisting of addition polymerization, condensation polymerization, and a combination thereof, providing at least one active agent, and assembling the polymer vesicle. In some embodiments, the active agent is a stimulator of interferon genes (STING) agonist or antagonist. In some embodiments, the active agent is a cyclic dinucleotide (CDN). In some embodiments, the active agent comprises at least one antigen and at least one cyclic dinucleotide (CDN).

Also provided, in some embodiments, is a method of administering an active agent to a cell, the method comprising administering a polymer vesicle loaded with the active agent to the cell, the polymer vesicle comprising a diblock copolymer including a hydrophilic first block and a second block including amine containing monomers and hydrophobic monomers. The second block forms an inner hydrophobic domain of a vesicle membrane and the hydrophilic first block forms a corona facing the exterior and aqueous interior of the vesicle membrane, the corona providing an outer shell that stabilizes the vesicle in aqueous media. The polymer vesicle enters an endosomal location within the cell and is destabilized at endosomal pH, thereby releasing the active agent within the cell. In some embodiments, the diblock copolymer comprises the formula [polyethylene glycol]$_m$b-[(2-diethylamino) ethyl methacrylate)$_x$-c-(butyl methacrylate)$_y$-c-(pyridyl disulfide ethyl methacrylate)$_z$]$_n$, where m is between 1 and 3 kDa, n is between 3 and 6 kDa, x is between 40 and 70 mole percent, y is between 30 and 60 mole percent, and z is between 2 and 16 mole percent. In one embodiment, m is 2 kDa and n is 4.5 kDa. In another embodiment, x is 57 mole percent, y is 35 mole percent, and z is 8 mole percent.

In some embodiments, the vesicle is stable at physiological pH, and is disassembled at a pH of about 6.5. In some embodiments, the vesicle is crosslinked. In some embodiments, the active agent is a stimulator of interferon genes (STING) agonist. In one embodiment, the active agent is a cyclic dinucleotide (CDN). In some embodiments, the polymer vesicle is administered to an organism. In one embodiment, the organism is a human. In some embodiments, the administration is by a route selected from the group consisting of intratumoral injection, intravenous (IV), subcutaneous, or a combination thereof. Other routes of administration may include oral, topical, cutaneous, transdermal, intradermal, intramuscular, intraperitoneal, intracranial, mucosal, transmucosal, intranasal, pulmonary, inhalation, direct intraventricular, rectal, intestinal, parenteral, intramedullary, intrathecal, intraocular, insufflation, intraarterial, and combinations thereof. In some embodiments, the cell is a cancer cell.

Further features and advantages of the presently-disclosed subject matter will become evident to those of ordinary skill in the art after a study of the description, figures, and non-limiting examples in this document.

BRIEF DESCRIPTION OF THE DRAWINGS

FIG. 5 shows a table summarizing the encapsulation efficiency of structurally and chemically diverse cargo into PEG-b-EBP polymer vesicles assembled from a bulk state. Encapsulation efficiency is defined as the percentage of cargo associated with the vesicle after cargo loading and separation of vesicles from unencapsulated cargo. N=number of experiments performed for a specific cargo type.

DESCRIPTION OF EXEMPLARY EMBODIMENTS

Figure 1:
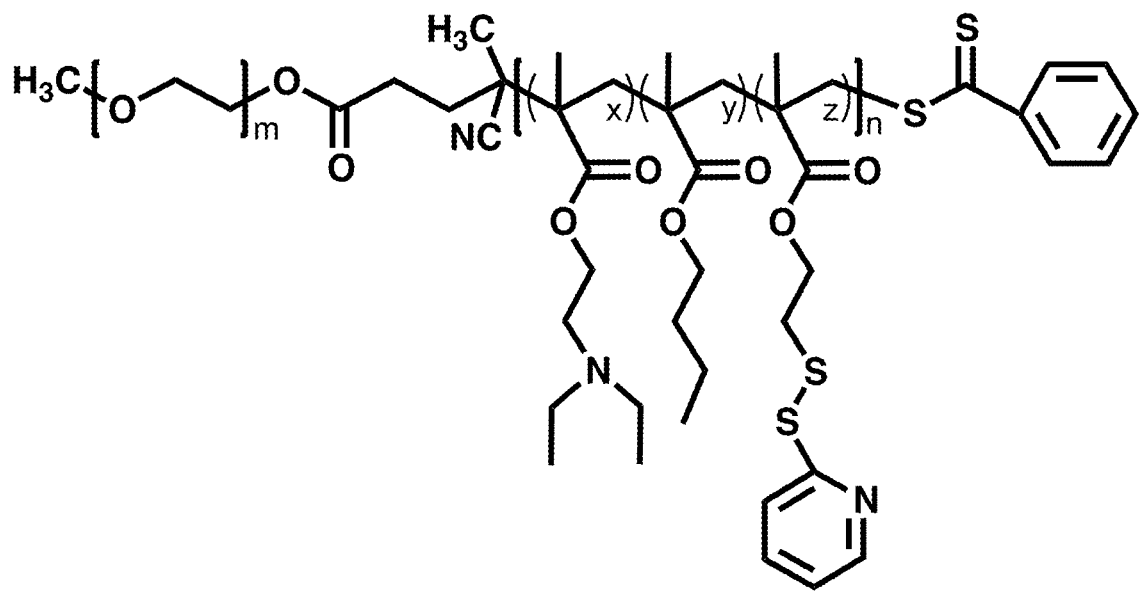
FIG. 1 shows the structure of a crosslinkable, pH-responsive copolymer used for assembly of polymer vesicles, according to an embodiment of the instant disclosure. m is the molecular weight of the hydrophilic block, n is the molecular weight of the terpolymer block, and x, y, and z are the molar composition of each respective monomer in the terpolymer block.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter includes polymers, polymeric vesicles, methods of forming polymeric vesicles, and methods of using polymeric vesicles. In some embodiments, a polymer comprises a diblock copolymer including a first block and a second block. In one embodiment, the first block and/or the second block are/is linear. In another embodiment, the diblock copolymer including the first block and the second block is linear. In a further embodiment, the diblock copolymer including the first block and the second block is crosslinked. Additionally or alternatively, in certain embodiments, the polymer including the first block and the second block is self-assembling, pH-responsive, membrane destabilizing, and/or endosome releasing.

The first block of the polymer disclosed herein is a hydrophilic block that includes any hydrophilic polymer suitable for copolymerization with the second block. Suitable polymers for the hydrophilic block include, but are not limited to, polyethers, polyesters, polycarbonates, polyvinyls, polyamino acids, polysulfobetaines, carboxybetaines, or combinations thereof. For example, the polyether compound may include, but is not limited to, polyethylene glycol (PEG). In one embodiment, the weight fraction of the hydrophilic block is between about 25% and about 35% of the total mass of the polymer. In another embodiment, the hydrophilic block has a molecular weight of at least about 1 kDa, at least about 2 kDa, at least about 3 kDa, at least about 5 kDa, at least about 10 kDa, at least about 15 kDa, at least about 20 kDa, between about 1 kDa and about 20 kDa, between about 1 kDa and about 15 kDa, between about 1 kDa and about 10 kDa, between about 1 kDa and about 5 kDa, between about 1 kDa and about 4 kDa, between about 1 kDa and about 3 kDa, or any combination, sub-combination, range, or sub-range thereof. In a further embodiment, for example, the hydrophilic block has a molecular weight of at least about 1 kDa, at least about 1.5 kDa, at least about 2 kDa, between about 1 kDa and about 3 kDa, between about 1.25 kDa and 2.75 kDa, between about 1.3 kDa and about 2.7 kDa, between about 1.5 kDa and about 2.5 kDa, between about 1.75 kDa and about 2.25 kDa, about 2 kDa, or any combination, sub-combination, range, or sub-range thereof.

The second block is a bipolymer or terpolymer block including at least one amine containing monomer, at least one hydrophobic monomers, and optionally at least one crosslinkable monomer. In certain embodiments, the diblock copolymer is crosslinked through the crosslinkable monomer in the terpolymer block. Suitable amine containing monomers include protonatable and/or tertiary amine containing monomers. In one embodiment, the amine containing monomers include any monomer with an amine group and a pKa of between about 4 and about 8. For example, the amine containing monomer may include (2-diethylamino) ethyl methacrylate (DEAEMA), 2-(dimethylamino)ethyl methacrylate, 2-(diisopropylamino)ethyl methacrylate, 2-N-morpholinoethyl methacrylate, 2-amino methacrylate hydrochloride, or a combination thereof. The hydrophobic monomers of the bipolymer or terpolymer block may include any hydrophobic monomers, such as, for example, acrylates, alkyl methacrylates, methacrylates with fluorinated or aromatic pendant groups, and/or related monomers. In some embodiments, for example, the alkyl methacrylates include, but are not limited to, butyl methacrylate (BMA), hexyl methacrylate, octyl methacrylate, decyl methacrylate, and/or lauryl methacrylate. Suitable crosslinkable monomers of the terpolymer block include, but are not limited to, pyridyl disulfide monomers, azide-functionalized monomers (e.g., crosslinkable with a bifunctional alkyne or cyclooctyne monomer via click chemistry), thiol-functionalized monomers (e.g., crosslinkable with bismaleimide), amine-functionalized monomers (e.g., crosslinkable with bifunctional active ester), photocrosslinkable monomers, or a combination thereof. One suitable pyridyl disulfide monomer includes, but is not limited to, pyridyl disulfide ethyl methacrylate (PDSMA). For example, in one embodiment, the terpolymer block includes ((2-diethylamino) ethyl methacrylate)-co-(butyl methacrylate)-co-(pridyl disulfide ethyl methacrylate), which is referred to herein as "EBP."

In some embodiments, a mole percent of the amine containing monomers in the second block is between about 40% and about 70%, between about 45% and about 65%, between about 50% and about 65%, between about 55% and about 60%, or any combination, sub-combination, range, or sub-range thereof. In some embodiments, a mole percent of the hydrophobic monomers in the second block is between about 30% and about 60%, between about 30% and about 55%, between about 30% and about 50%, between about 30% and about 45%, between about 30% and about 40%, or any combination, sub-combination, range, or sub-range thereof. For example, in one embodiment, the second block includes a DEAEMA to BMA ratio of about 60:40. In some embodiment, a mole percent of the crosslinkable monomers in the terpolymer block is between about 1% and about 16%, between about 2% and about 16%, between about 2% and about 14%, between about 4% and about 12%, between about 6% and about 10%, between about 7% and about 9%, or any combination, sub-combination, range, or sub-range thereof. For example, the terpolymer block may include DEAEMA:BMA:PDSMA at a ratio of 57:35:8, 57:39:4, or any other suitable ratio of monomers within the ranges disclosed herein. In some embodiments, the second block including the amine containing monomers, hydrophobic monomers, and optionally the crosslinkable monomers has a molecular weight of up to about 40 kDa, up to about 30 kDa, between about 1 kDa and about 40 kDa, between about 1 kDa and about 30 kDa, between about 1 kDa and about 20 kDa, between about 1 kDa and about 10 kDa, between about 1 kDa and about 6 kDa, between about 3 kDa and about 6 kDa, or any combination, sub-combination, range, or sub-range thereof. In some embodiments, the second block including the amine containing monomers, hydrophobic monomers, and optionally the crosslinkable monomers has a molecular weight of between about 3 kDa and about 6 kDa, between about 3.5 kDa and about 5.5 kDa, between about 4 kDa and about 5 kDa, about 4.5 kDa, or any combination, sub-combination, range, or sub-range thereof.

Together, the hydrophilic first block and the second block described above form a low molecular weight diblock copolymer having the general formula [hydrophilic block]$_m$-[second block]$_n$, where m is the molecular weight of the hydrophilic block and n is molecular weight of the second block. For example, in one embodiment, the low molecular weight diblock copolymer has the formula PEG$_m$-EBP$_n$, where m is between 1 and 3 kDa and n is between 3 and 6 kDa. In another embodiment, the low molecular weight diblock copolymer has the formula [hydrophilic block]$_m$-b-[(amine containing monomer)$_x$-(hydrophobic monomer)$_y$-c-(crosslinkable monomer)$_z$]$_n$, where x is the mole percent of the amine containing monomer in the second block, y is the mole percent of the hydrophobic monomer in the second block, and z is the mole percent of the crosslinkable monomer in the second block. In a further embodiment, x is between 40% and 0.70% (i.e., a mole fraction of between 0.40 and 0.70), y is between 30% and 60% (i.e., a mole fraction of between 0.30 and 0.60), and z is between 0% and 16% (i.e., a mole fraction of between 0.00 and 0.16). In certain embodiments, when the second block is a terpolymer block, z is between 2% and 16% (i.e., a mole fraction of between 0.02 and 0.16). For example, as illustrated in FIG. 1, one specific low molecular weight diblock copolymer has the formula [mPEG]$_m$b-[DEAEMA$_x$-c-BMA$_y$-c-PDSMA$_z$]$_n$, where m is 2 kDa, n is 4.5 kDa, x is 0.57, y is 0.35, and z is 0.08.

Figure 2:
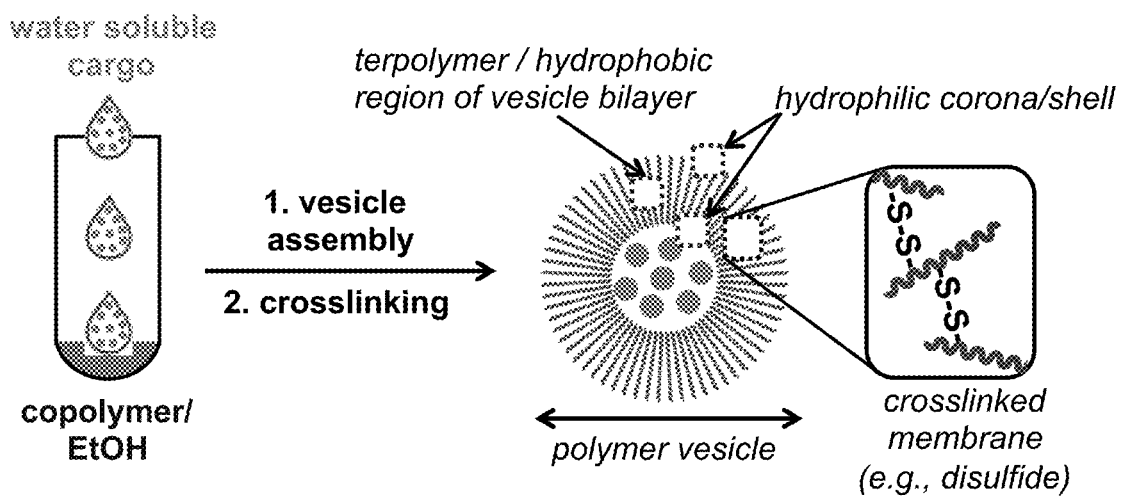
FIG. 2 shows a schematic view of a process by which polymer vesicles are assembled from a bulk phase and loaded with water soluble cargo. The enlarged view shows an example of a crosslinked membrane according to an embodiment of the disclosure.

In some embodiments, the diblock copolymer forms a self-assembling polymer vesicle (FIG. 2). In such embodiments, the hydrophilic block forms a corona that faces the exterior and aqueous interior of the vesicle, and the second block forms a hydrophobic inner region of the vesicle membrane. The corona formed by the hydrophilic block provides a shell that stabilizes the polymer vesicle in aqueous media. In one embodiment, before and/or after self-assembly, the polymer vesicle is crosslinked. In another embodiment, the post-assembly crosslinking is performed in situ. In a further embodiment, the post-assembly crosslinking increases the molecular weight of the polymer chains, forming a high molecular weight polymersome (e.g., greater than 8 kDa) from the low molecular weight diblock copolymer (e.g., less than 8 kDa). The diameter of the polymer vesicle is between 50 and 1000 nm, between 50 and 500 nm, between 50 and 250 nm, between 50 and 100 nm, less than 100 nm, or any combination, sub-combination, range, or sub-range thereof.

Figure 3:
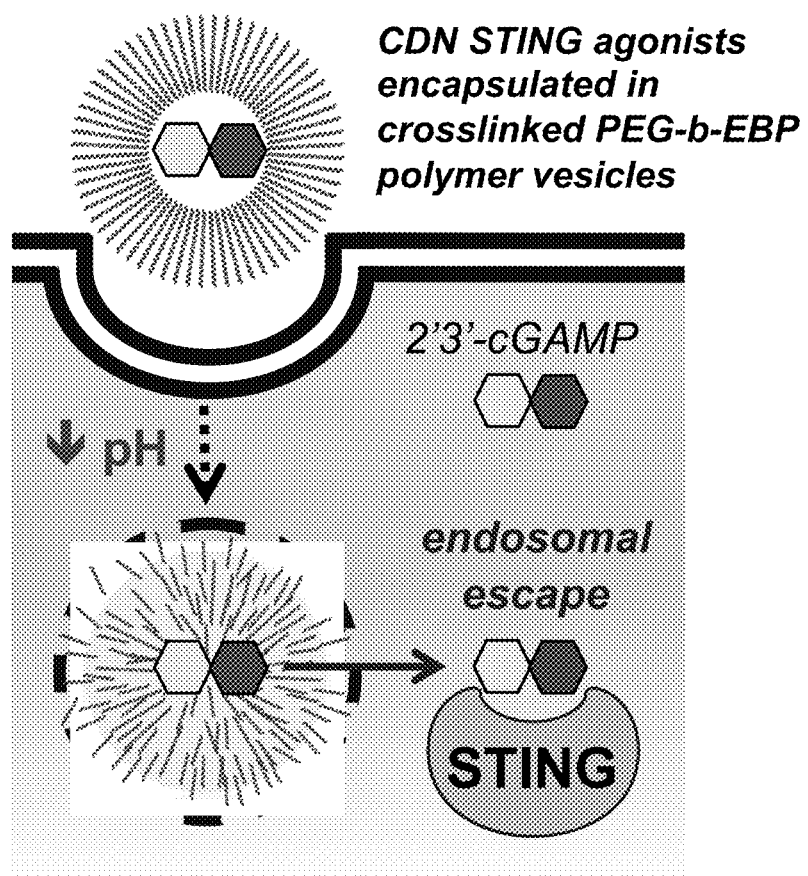
FIG. 3 shows a scheme demonstrating the process by which polymer vesicles disassemble in response to decreasing endosomal pH to unveil membrane-destablizing polymer chains that promote the release of encapsulated cargo (here, cGAMP) from endosomes or lysosomes into the cytosol for binding to cytosolic targets, including STING.
Figure 4:
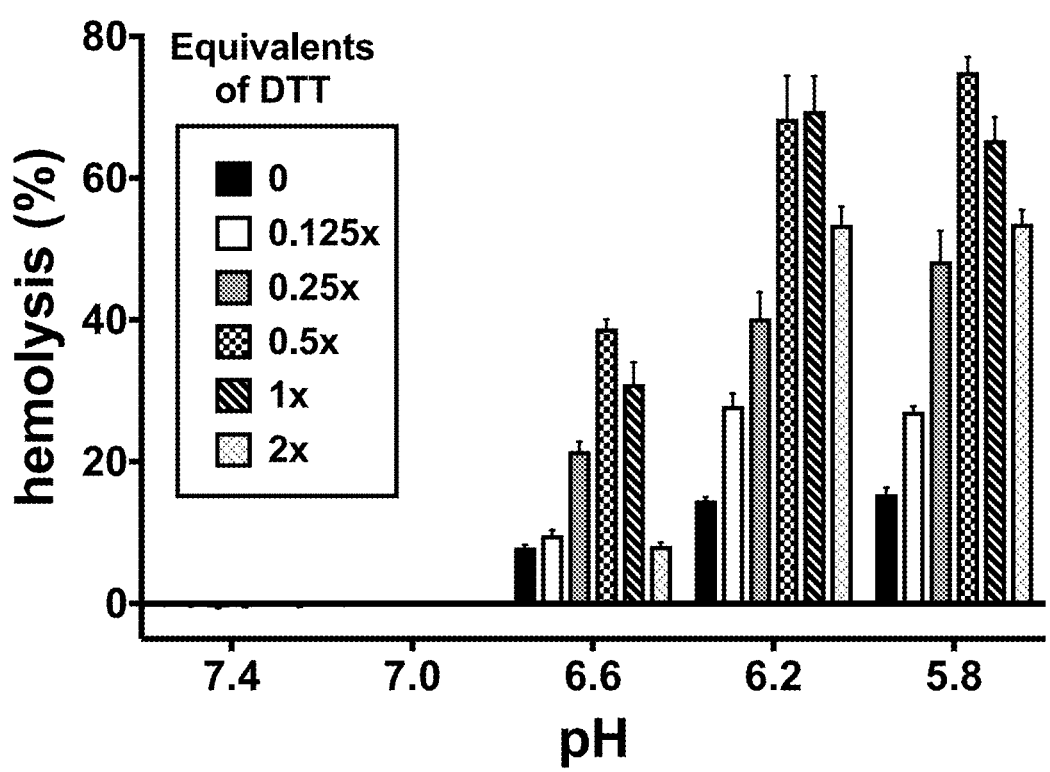
FIG. 4 shows a graph illustrating DTT reduction dependence on PEG-EBP polymer vesicle mediated hemolysis. Samples were run in quadruplicate at a polymer concentration of 10

In some embodiments, the polymer vesicle is a stealth, pH-responsive vesicle that is endosomolytic via direct membrane interaction mechanisms. For example, in one embodiment, the polymer vesicle is surface neutral and/or has a near neutral zeta potential. In another embodiment, the vesicle disassembles at a specific pH value, permitting the polymer chains to destabilize lipid bilayer membranes (e.g., endosomal membranes) in the proximity thereof (FIG. 3). In a further embodiment, the second block is shielded by the hydrophilic block at a first pH (e.g., a physiological pH of about 7.4), only becoming active when exposed to a second pH (e.g., acidic environment, such as a pH 6.5 or below). Without wishing to be bound by theory, it is believed that the crosslinking of the polymersome increases and/or enhances a pH-dependent membrane-destabilizing activity of the polymersome (FIG. 4). Accordingly, the pH responsive behavior can be precisely tuned through control of monomer composition in the second block as well as the degree of crosslinking, which permits tailoring of properties for specific applications.

In certain embodiments, the polymer vesicle is loaded with one or more active agents. The term "active agent," as used herein, refers to any compound used for the treatment or diagnosis of a disease. Suitable active agents include, but are not limited to, compounds that rely on intracellular access, compounds that rely on access to cytosolic receptors/pathways, stimulator of interferon genes (STING) agonists or antagonists such as cyclic dinucleotides (CDN), oligonucleotides, proteins, polysaccharides, peptides, lipopeptides, hydrophobic and amphiphilic small molecular drugs, antibodies, nanobodies, RNA, mRNA, miRNA, siRNA, aptamers, antibiotics, antigens (e.g., tumor antigens, tumor neoantigens), chemotherapeutics, imaging agents, quantum dots, any other suitable compound for disease treatment, or a combination thereof.

In one embodiment, for example, the active agent includes one or more CDNs or other STING pathway agonists. STING (also known as TMEM173, MITA, EMS, and MPYS) is a transmembrane endoplasmic reticulum (ER) protein that undergoes a conformational change in response to direct binding of cyclic dinucleotides (CDNs), resulting in a downstream signaling cascade involving TBK1 activation, IRF-3 and/or STATE phosphorylation, and production of IFN-β and other cytokines. The STING pathway in tumor-resident host antigen presenting cells is involved in the induction of a spontaneous CD8+ T cell response against tumor-derived antigens. Specific CDNs include, but are not limited to, 2'3'-cGAMP, c-di-GMP, 2'3'-cGAM(PS)$_2$ (Rp/Sp), and c-[2'FdGMP]-[2'FdAMP]. STING agonists and CDNs, and uses thereof, include without limitation those described in U.S. Pat. Nos. 7,709,458, 7,592,326, 8,450,293, 9,315,523, 9,549,944, and 9,597,391; and PCT Publication Nos. WO 2011/003025, WO 2014/093936, WO 2014/099824, WO 2014/189805, WO 2014/179335, WO 2014/179760, WO 2015/074145, WO 2016/096174, WO 2016/096577, WO 2016/120305, WO 2016/145102, WO 2017/027645, WO 2017/027646, and WO 2017/075477, the disclosures of which are hereby incorporated by reference as it relates to CDNs and their use.

In some embodiments, the polymers and/or polymer vesicles disclosed herein provide increased loading and/or loading efficiency in endosomolytic vesicles as compared to existing compositions and methods. For example, assembly of polymer vesicles from low molecular weight polymer chains (e.g., 8 kDa or less) in a highly concentrated or bulk state according to the compositions and methods described herein may provide higher loading as compared to existing methods. The term "loaded" or "loading" refers to incorporation of cargo, such as an active agent, in and/or on the polymer vesicle, including, but not limited to, encapsulation of active agent(s), association of active agent(s) with the polymer vesicle membrane, any other suitable incorporation of the active agent(s), or a combination thereof. In one embodiment, for example, water soluble active agents, such as CDNs, ovalbumin, dextran, peptides, oligonucleotides, and/or any other water soluble active agents, are encapsulated in the core of the polymer vesicle. In another embodiment, anionic active agents, such as CDNs, CpG ODN, 5'ppp-dsRNA, or any other anionic active agent, are encapsulated in the core of the polymer vesicle and/or associated with positively charged groups of the vesicle membrane. In a further embodiment, hydrophobic and/or amphiphilic active agents, such as the toll-like receptor (TLR)-2 agonist $Pam_3CSK4$, are loaded into the polymer vesicle membrane. Additionally or alternatively, the hydrophilic block of the polymer may be functionalized with reactive groups, including, but not limited to, biotin, azide, maleimide, aldehyde, ketone, alkyne, alkene, amino, carboxylic acid, hydroxyl, and/or pyridyl disulfide for conjugation of cargo to the surface of the vesicle.

As will be appreciated by those skilled in the art, different types of cargo may be simultaneously loaded into and/or onto the polymer vesicle through one or more of the methods disclosed herein. FIG. 5 provides a summary of encapsulation efficiencies obtained for a diversity of cargo as described above. The simultaneous loading of different types of cargo provides combination loading of chemically diverse cargo. For example, different types of cargo may be simultaneously encapsulated in, associated with, or conjugated to a single polymer vesicle. In another example, chemically diverse cargo may be loaded through a combination of encapsulation, association with the vesicle membrane, and/or conjugation to the surface of the vesicle.

When loaded, the polymer vesicles increase cellular uptake and/or cytosolic delivery of the one or more loaded active agents as compared to delivery of the active agent alone or with existing compositions. In some embodiments, for example, the formation of polymer vesicles from low molecular weight copolymers provides a higher capacity for endosomal rupture and associated cytosolic delivery after crosslinking of the vesicle membrane. Additionally or alternatively, the pH-responsive and/or membrane destabilizing properties of the polymer vesicle may facilitate and/or increase escape of the vesicle-associated cargo from endo-lysosomal trafficking. For example, in one embodiment, the polymer vesicle is stable at first pH, such as a physiological pH (e.g., about 7.4), and disassembles at a lower pH, such as an acidic pH (e.g., less than 6.6). In another embodiment, the polymer vesicles are stable upon administration, but as the vesicle subsequently encounters a lower pH environment (e.g., following endocytosis and/or in certain tumor types), the amino groups in the terpolymer group become more protonated. Higher protonation increases the aqueous solubility of the terpolymer block and, therefore, the vesicle assembly is no longer energetically favorable, resulting in disassembly of the vesicle into soluble polymer chains or other morphologies (e.g., micelles). This process releases encapsulated cargo and permits the protonated terpolymer block to disrupt the endosomal membrane, which increases delivery of cargo to cytosolic targets.

Figure 6A:
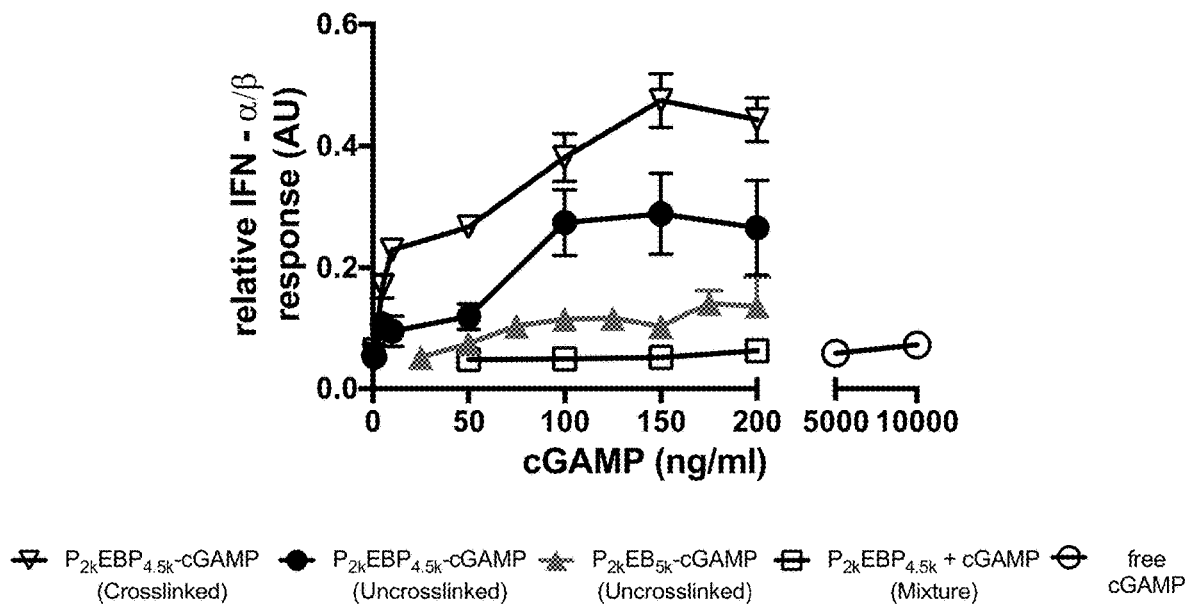
FIGS. 6A-C show graphs illustrating enhanced in vitro cGAMP potency when encapsulated in various PEG-EB and PEG-EBP polymer vesicle formulations. X-cGAMP: encapsulated in particle formulation. X+cGAMP: physically mixed with particle formulations. (A) THP1-Blue ISG cells: 10000 cells/well, 24 hr treatment. Relative response to cGAMP determined via interferon regulatory factor inducible secreted embryonic alkaline phosphatase reporter construct. (B) RAW-Blue ISG cells: 50000 cells/well, 24 hr treatment. Relative response to cGAMP determined via interferon regulatory factor inducible secreted embryonic alkaline phosphatase reporter construct. (C) DC 2.4 dendritic cells: 10000 cells/well, 24 hr treatment. IFN-α response determined via ELISA.
Figure 6B:
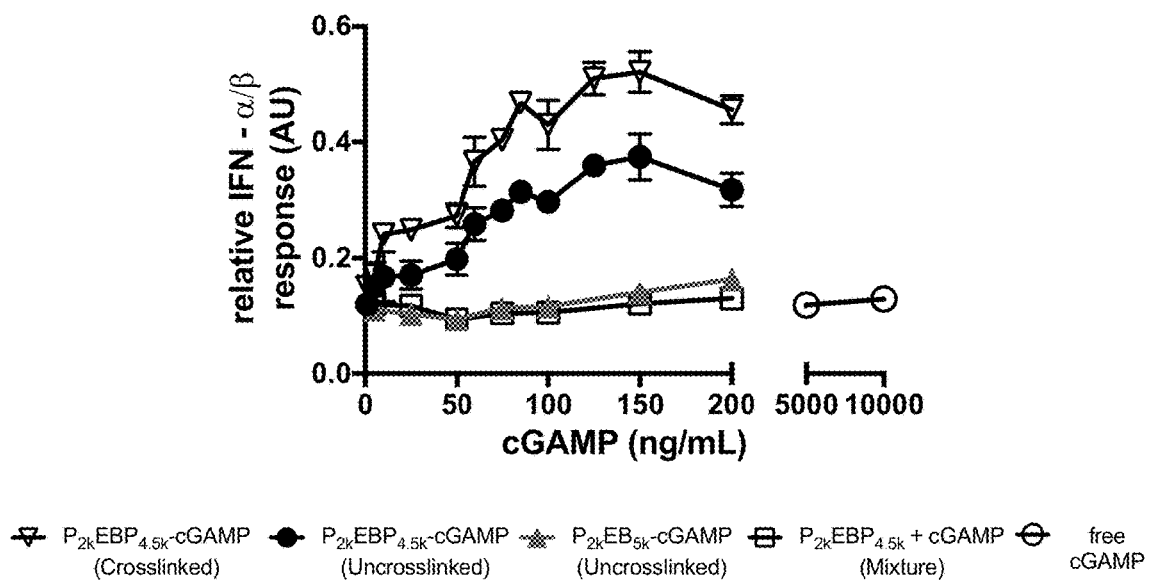
Figures 6C, 7A:
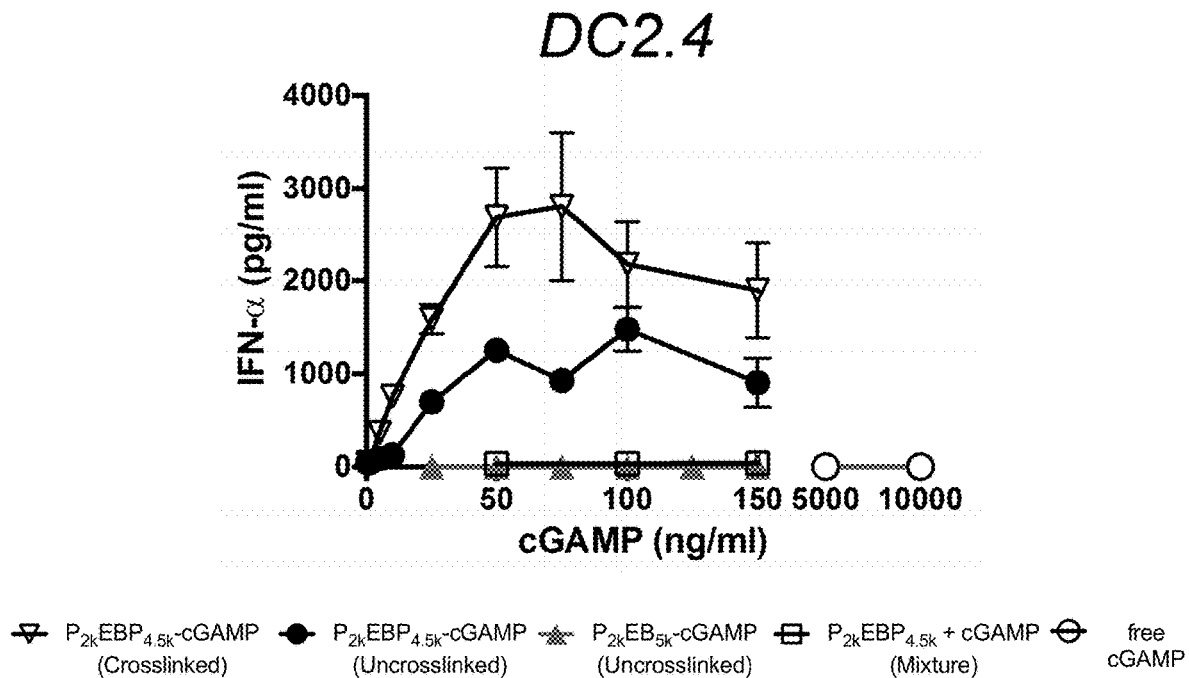
FIGS. 7A-B show a table and images illustrating properties of polymers according to embodiments disclosed herein. (A) Shows a table describing the properties of a subset of PEG-b-EB polymers used for self-assembly of colloids from a bulk state. The molecular weight of each block is described along with the associated weight percentage of the hydrophilic block. The morphology of the resultant colloid was then characterized by transmission electromicroscopy and the polymers were determined to form vesicles (V), non-stable aggregates (A), cylindrical micelles (C), spherical micelles (S), or a mixture of structures (indicated by an /). (B) Shows representative TEM images of colloids resulting from self-assembly of several polymers described in the table.

These pH-responsive and/or membrane destabilizing properties may be selected, such as through dipolymer or terpolymer block composition and/or degree of crosslinking, to provide a desired amount of cargo accumulation and/or release into the cytosol. Accordingly, in some embodiments, the activity of the loaded active agents, such as those that rely on access to cytosolic receptors/pathways, may be controlled and/or increased through in situ crosslinking of the vesicle membrane. For example, where the vesicle-associated cargo includes CDNs such as cGAMP, controlling and/or increasing release of CDNs into the cytosol controls and/or increases delivery of the CDNs to their cytosolic targets, such as stimulator of interferon genes (STING) (FIGS. 6A-C). Although described above with respect to delivery of CDNs, as will be appreciated by those skilled in the art, the instant disclosure is not so limited and may include controlled and/or targeted delivery of any other suitable cargo and/or active agent. One example includes targeted gene delivery (e.g., siRNA, mRNA, DNA, etc.). Other examples include, but are not limited to, delivery of CDNs to cells of the immune system (immune cells), including both murine and human macrophages, dendritic cells, and cancer cells; delivery of immunostimulatory DNA to immune cells; delivery of protein and peptide antigens to murine dendritic cells to increase antigen presentation on class I MHC as assessed in cross presentation assays; in vivo delivery of protein and peptide antigens using mouse models with downstream quantification of T cell responses via MHC tetramer staining, intracellular cytokine staining, and ELISPOT and antibody titers via ELISA; in vivo delivery of CDNs in murine cancer models; and/or combination encapsulation of hydrophilic/hydrophobic cargo. The polymer vesicles may also provide combination delivery of chemically diverse cargo, such as, but not limited to, cytosolic delivery of vaccine antigen/adjuvant combinations.

Also provided herein are methods of forming polymers and polymer vesicles. The polymers may be formed by any suitable polymerization technique, including, but not limited to, bulk polymerization, solution polymerization, suspension polymerization, emulsion polymerization, melt polymerization, solution polycondensation, other addition polymerization techniques, other condensation techniques, plasma polymerization, or a combination thereof. In some embodiments, the polymers are synthesized by reversible addition-fragmentation chain transfer (RAFT) polymerization. As is understood by those skilled in the art, RAFT polymerization is a controlled radical polymerization technique where a chain transfer agent mediates polymerization through a reversible chain-transfer process. For example, in one embodiment, the hydrophilic block is attached to the chain transfer agent, followed by introduction of free radicals. The introduction of the free radicals fragments a carbon-sulfur bond adjacent to a dithioate, generating a free radical on a released PEG containing molecule. Monomers are then added on during the polymerization process to form the desired polymer, after which various byproducts may be removed by precipitation and/or dialysis.

During RAFT polymerization the monomers are believed to add stochastically, forming the polymer including chemically different individual polymer chains having total average properties defined by the polymer feed and reaction kinetics of individual monomers. Accordingly, the composition/concentration of monomers in the polymer feed (i.e., what is added in the reaction) is selected to provide the desired properties of the polymer. For example, in one embodiment, the ratio of monomers in the polymer feed is selected to provide the desired ratio of amine containing, hydrophobic, and/or crosslinkable monomers in the resulting polymer. In another embodiment, the choice of monomer and monomer composition is modulated to permit tuning of pH-responsive properties and membrane destabilizing activity. In a further embodiment, the crosslinking is tuned to control pH-dependent membrane destabilization/endosomal disruption to influence cargo localization within intracellular components. Crosslinking also increases hemolytic activity of terpolymer block compositions with pH-dependent membrane destabilizing activity (e.g., hemolysis). In certain embodiments, such as, for example, when the polymer includes linear PEG-b-(DEAEMA-c-BMA-c-PDSMA) chains crosslinked through disulfide bonds via partial reduction of PDSMA groups, the crosslinking may be achieved and/or controlled through partial reduction of PDS groups with dithiothreitol (DTT).

Following polymerization, the polymer vesicles may be assembled through solution and/or bulk phase processes. In one embodiment, solution phase assembly of the polymer vesicles includes dissolution of the polymer in an acidic aqueous medium followed by titration to pH 7.4 with basic solution, or dissolution of polymer in a water miscible organic solvent followed by dropwise transfer to a neutral aqueous medium. The hydrophilic blocks used in solution phase assembly have a molecular weight of at least about 1 kDa, preferably between about 1 kDa and about 20 kDa. In another embodiment, bulk phase assembly includes dissolving the polymer in a low amount of organic solvent, such as, for example, 5 µg of polymer in 4 µL of ethanol. When loading hydrophobic active agent(s), the active agent(s) are first dissolved in the organic solvent, which is then used to co-dissolve the polymer. Additionally or alternatively, with hydrophilic or amphiphilic active agent(s), an equivalent volume of water containing the active agent(s) is added to the polymer. The hydrophilic blocks used in bulk phase assembly have a molecular weight of at least about 1 kDa, preferably between about 1 kDa and about 3 kDa.

Next, the mixture is vortexed and allowed to equilibrate, forming a gel. Three equivalent volumes of 25% organic: 75% water solution are then added to the gel, followed by centrifugation and equilibration. Although described above with regards to volumes of 25% organic:75% water, as will be appreciated by those skilled in the art, the disclosure is not so limited and may include other volumes such as, but not limited to, between about 0% and about 40% organic. After centrifugation and equilibration, excess de-ionized water is added to the gel, followed by ultrasonication and mechanical disaggregation (vortexing) of the polymer gel. A reducing agent, such as DTT or tris(2-carboxyethyl)phosphine (TCEP), is then added to the colloid and allowed to react for at least 30 minutes. The reducing agent is provided at any suitable concentration including, but not limited to, 0.5 molar equivalents. Once the reducing agent has been added and allowed to react, the colloid is purified and then buffered immediately prior to use. Purification includes dialysis, ultrafiltration, or any other suitable method of purification. Buffering solutions include, but are not limited to, phosphate-buffered saline (PBS).

Without wishing to be bound by theory, in some embodiments, it is believed that loading/encapsulation of the cargo occurs during one or more of the equilibration steps, when lamellar structure is believed to unbind and begin to fluctuate into a sponge phase before closing into close packed vesicles. Alternatively, in some embodiments, it is believed that loading/encapsulation of the cargo occurs during the final dilution into excess water and/or sonication steps.

Figure 7B:
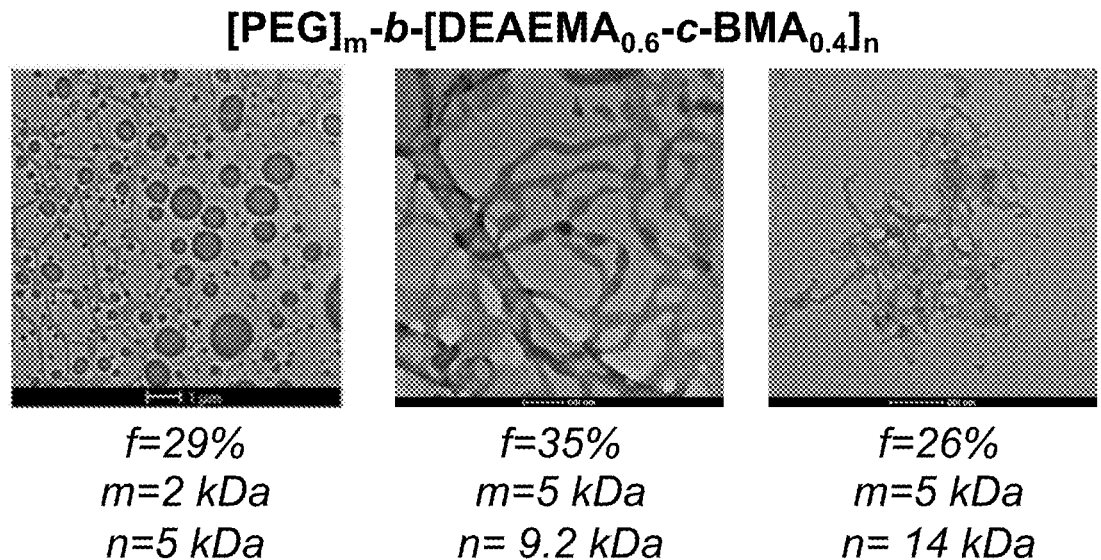

While bulk assembly forms polymer vesicles with a hydrophilic block including a weight fraction of between 25% and 35% of the total mass of the polymer vesicle, weight fractions outside of this range are incapable or show reduced efficiency in the formation of vesicles, instead forming aggregates and other self-assembled structures (e.g., micelles) (FIGS. 7A-B). Additionally or alternatively, a hydrophilic block molecular weight of at least 2 kDa and a terpolymer block molecular weight of between 4 and 5 kDa provide efficient vesicle assembly from bulk phase, while weight fractions outside of this range generate increased amounts of aggregates and other self-assembled structures.

Notably, this approach allows for high yield self-assembly of polymer vesicles from the bulk state due to the low average chain molecular weights, avoiding low encapsulation efficiencies that are associated with self-assembly from the solution phase. In some embodiments, active agent(s), such as CDNs, are encapsulated at efficiencies ranging from 25% to 60% or more (FIG. 5). In addition, post-assembly crosslinking increases the effective chain molecular weight (FIG. 8A), allowing for endosome destabilizing properties that are generally associated with high molecular weight chains. Furthermore, in some embodiments, crosslinked nanoparticles deliver active agent(s) to the cytosol more efficiently than uncrosslinked analogues. In certain embodiments, delivery of active agent(s), such as CDNs, with crosslinked vesicles increases active agent activity by at least 100 to 1000× in cell culture models (FIGS. 6A-C and 9A-B). Accordingly, this processing method provides high yield encapsulation of chemically diverse molecules in polymeric vesicles that are capable of efficiently delivering active agent(s) to cytosolic targets.

The high yield encapsulation and/or increased delivery efficiency provided by the polymer vesicles facilitates disease treatment with various individual or combined active agent(s). Accordingly, also provided herein is a method of administering one or more active agents to a cell or organism (e.g., a human), the method including administering a polymer vesicle loaded with one or more active agents. Further provided herein is a method of treating a disease, the method including administering an effective amount of a polymer vesicle loaded with one or more active agents to a cell or organism in need thereof.

As used herein, the term "effective amount" refers to an amount that, when administered alone or in combination with an additional therapeutic agent to a cell, tissue, or subject, is effective to cause a measurable improvement in one or more symptoms of disease, for example cancer or the progression of cancer. An effective dose further refers to that amount of an agent sufficient to result in at least partial amelioration of symptoms, e.g., tumor shrinkage or elimination, lack of tumor growth, increased survival time. When applied to an individual active ingredient administered alone, an effective dose refers to that ingredient alone. When applied to a combination, an effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity. Determination of the effective amount is preferably made by the clinician, e.g., using parameters or factors known or suspected in the art to affect treatment. Generally, the dose may begin with an amount somewhat less than the optimum dose and then increased by small increments thereafter until the desired or optimum effect is achieved relative to any negative side effects. Important diagnostic measures include those of symptoms of, e.g. in the case of a STING agonist, the inflammation or level of inflammatory cytokines produced.

The loaded polymer vesicles may be administered through any suitable route including, but not limited to, intratumoral injection, intravenous (IV), subcutaneous, or a combination thereof. Other routes of administration may include oral, topical, cutaneous, transdermal, intradermal, intramuscular, intraperitoneal, intracranial, mucosal, transmucosal, intranasal, pulmonary, inhalation, direct intraventricular, rectal, intestinal, parenteral, intramedullary, intrathecal, intraocular, insufflation, intra-arterial, or a combination thereof. For example, in one embodiment, intratumoral injection of encapsulated 2'3'-cGAMP is more effective than free cGAMP in mediating tumor regression, improving mouse survival, and generating immune memory that protects against tumor re-challenge in mouse tumor models. In another embodiment, intratumoral injection of encapsulated CDNs improves the therapeutic efficacy of checkpoint blockade (e.g., anti-PD1, anti-PD-L1, and/or anti-CTLA-4) in mouse tumor models. In a further embodiment, administration of encapsulated CDNs improves the therapeutic efficacy of indoleamine 2,3-dioxygenase (IDO) inhibitors, including, but not limited to, indoximod, epacadostat, any other suitable IDO inhibitor, and combinations thereof.

Figure 11:
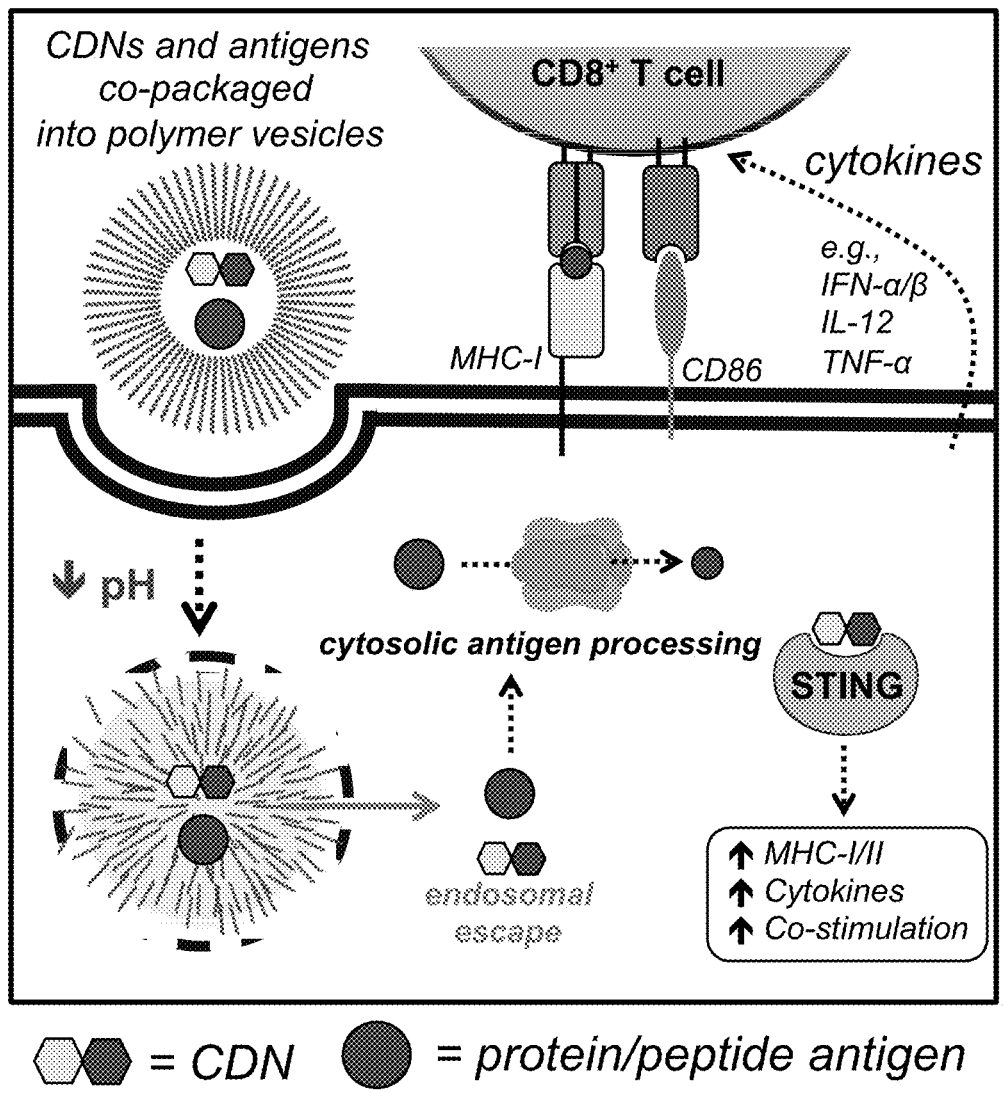
FIG. 11 shows an illustration describing how co-encapsulation of CDN STING agonists and protein/peptide antigens into endosome-destabilizing polymer vesicles can be used as a vaccine for generating cellular immunity. Co-packaging of CDN and antigen promotes cytosolic dual-delivery of antigen and CDN into the same cell, which allows antigen to be processed by cytosolic antigen processing machinery for more efficient presentation on major histocompatibility complex class-I (MHC-I), while cytosolic delivery of CDNs increases adjuvant potency, resulting in increased antigen presentation, expression of co-stimulatory molecules, and cytokines.
Figure 12A:
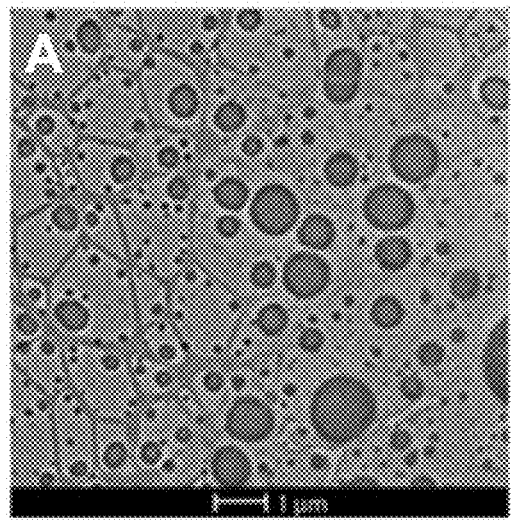
FIGS. 12A-D show graphs and images illustrating PEG-EBP polymer vesicle properties. (A) Transmission electron microscopy, (B) cryo-transmission electron microscopy, (C) dynamic light scattering, and (D) zeta potential measurement.
Figure 12B:
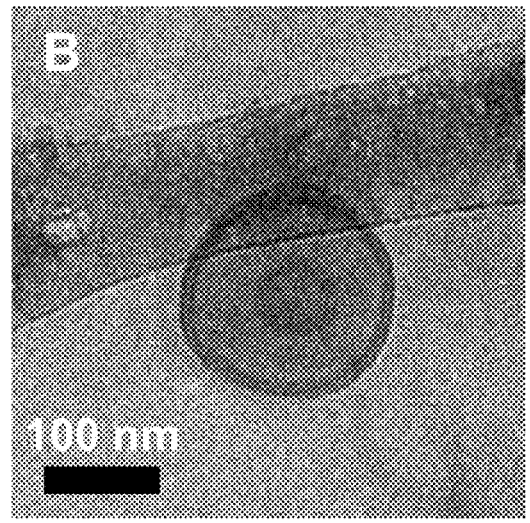
Figure 12C:
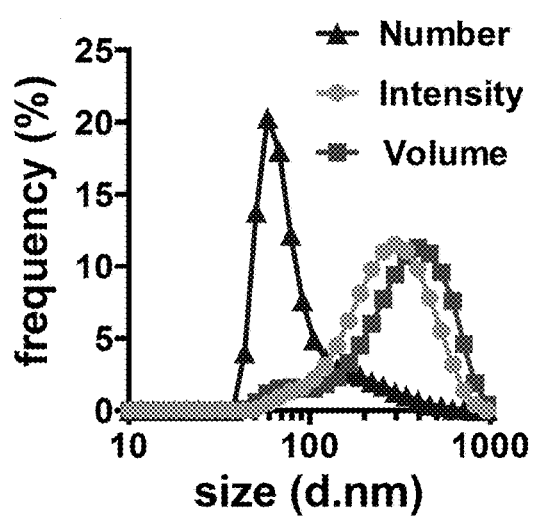
Figure 12D:
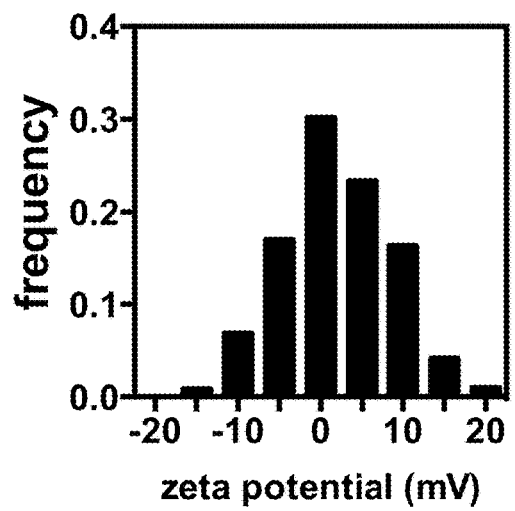

As will be understood by those skilled in the art, the frequency of administration may be determined by the type of active agent, the concentration of active agent, and/or the purpose of administration. In some embodiments, the loaded vesicles disclosed herein may be administered by continuous infusion or by doses administered. Doses administration includes, but is not limited to, daily, 1-7 times per week, weekly, bi-weekly, monthly, bimonthly, quarterly, semiannually, annually, or any other suitable frequency. For example, in certain embodiments, the encapsulated CDNs can be delivered via an intravenous (IV) route at a dose of at least 25 µg/mouse without adverse systemic effects (FIGS. 10A-D). Although primarily described herein with regards to cancer/tumor treatment, as will be appreciated by those skilled in the art, the disclosure is not so limited and includes any other treatment or application for which intracellular delivery of active agent(s) is suitable. One other application includes vaccines, such as, for example, delivery of CDNs co-encapsulated with protein and/or peptide antigens (FIG. 11). In some embodiments, the co-encapsulation of CDNs and protein/peptide antigens provides increased antigen delivery and/or increased antigen presentation.

EXAMPLES

Example 1

In this example, polymeric vesicles are prepared from a poly[(ethylene glycol)-b-[(pyridyl disulfide ethyl methacrylate)-co-((2-diethylamino) ethyl methacrylate)-co-(butyl methacrylate)] diblock polymer (PEG-EBP) (FIG. 1). A combination of polymer design and formulation process result in production of surface neutral, pH responsive, and membrane destabilizing vesicles that can encapsulate cyclic guanosine monophosphate-adenosine monophosphate (cGAMP) with encapsulation efficiencies of 38±3%. PEG-EBP encapsulated cGAMP is significantly more potent than free cGAMP and is used for treatment of melanoma and neuroblastoma tumors in murine models.

Discussion

This example describes the high concentration formulation from a bulk state and post assembly crosslinking of low molecular weight $PEG_{2k}$-$EBP_{4.5k}$ polymer chains for high encapsulation efficiency and enhanced potency of the cGAMP compound.

Poor cGAMP localization in the cytosolic compartments of tumor associated cells is a significant barrier to the potential of cGAMP based cancer immunotherapy. The following describes a combination of polymer synthesis and formulation processes that result in pH responsive and membrane interactive polymeric vesicles that are capable of encapsulating cGAMP and facilitating its delivery to its endogenous sensor, the cytosolic STING protein. The $PEG_{2k}$-b-$EBP_{4.5k}$ polymer was synthesized via reversible addition-fragmentation chain-transfer (RAFT) polymerization with a molar composition of 57% (2-diethylamino) ethyl methacrylate, 35% butyl methacrylate, and 8% pyridyl disulfide ethyl methacrylate comprising the EBP polymer block. For formulation of polymeric vesicles, 5 mg of the polymer is mixed with 4 µL of ethanol. Upon equilibration, 4 µL of cGAMP solution (0-50 mg/mL in water) is added to the polymer/ethanol gel. The system is again allowed to equilibrate, followed by a second addition of 12 µL of 25% $EtOH/H_2O$ mixture. Finally, 30 µL of 33% $EtOH/H_2O$ mixture is added to the polymer gel, followed by sonication at 40° C. Upon formation of vesicles, the colloid is diluted into water and sonicated further to generate the PEG-EBP encapsulated cGAMP colloid.

Solvent composition and stepwise addition amounts were chosen to maximize the vesicle yield of the formulation process while maximizing encapsulant concentration during vesicle self-assembly. This process results in encapsulation efficiencies of cGAMP within PEG-EBP vesicles of 38±3%, as determined via high performance liquid chromatography. Particles were crosslinked post assembly via addition of 0.5 molar equivalents of DTT relative to pyidyl disulfide moieties comprising the PEG-EBP colloid. Nanoparticles were readily separated from free cGAMP and crosslinking byproducts via centrifugal ultrafiltration using a 10 kDa cutoff.

Figure 8A:
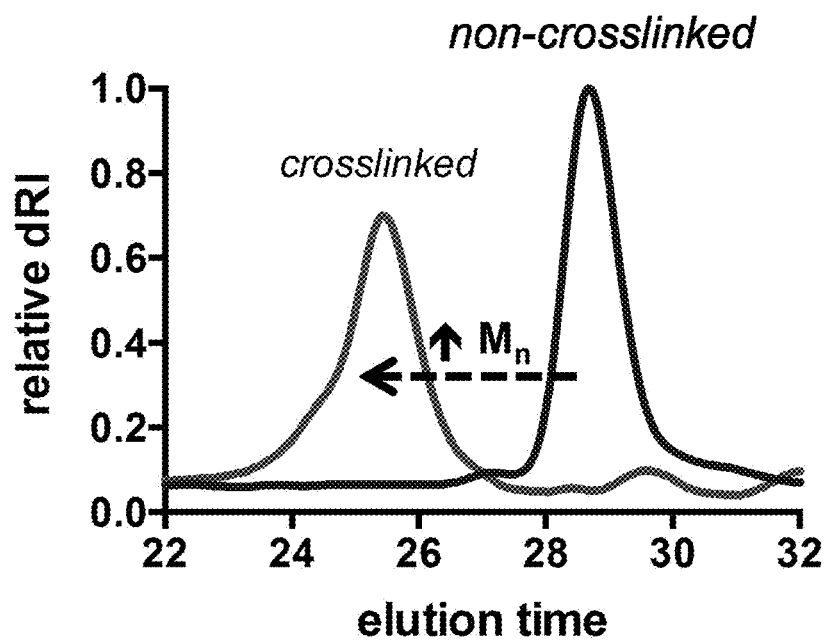
FIGS. 8A-C show graphs illustrating molecular weight and particle size/disassembly of polymers according to embodiments disclosed herein. (A) Shows a size exclusion chromatogram demonstrating the increase in polymer chain molecular weight that occurs upon in situ crosslinking of the vesicle membrane. (B-C) Show dynamic light scattering (DLS) data demonstrating a reduction in particle size and/or particle disassembly in response to decreasing the pH of the surrounding media. Neither particle size nor pH-responsive behavior is significantly different between (B) non-crosslinked or (C) optimally crosslinked (0.5 equivalents of DTT) PEG-EBP polymer vesicles.
Figure 8B:
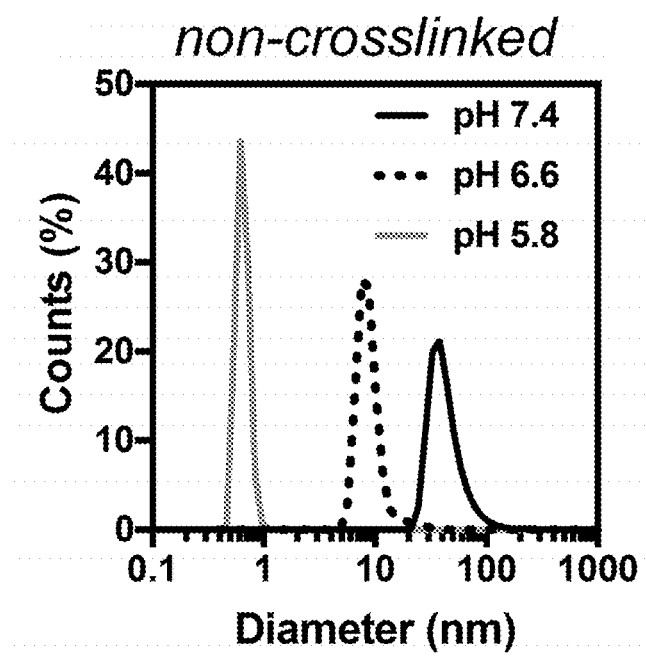
Figure 8C:
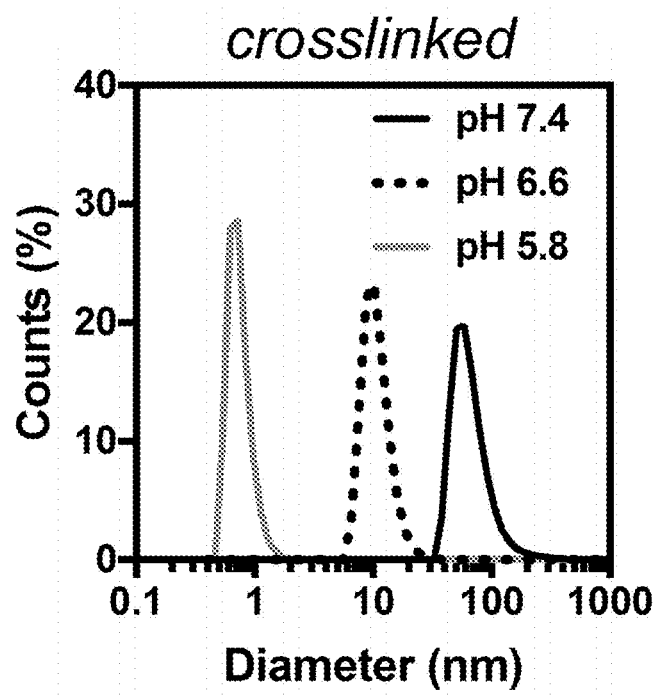

Dynamic light scattering and zeta potential experiments indicated that vesicles are surface neutral, largely less than 100 nm in diameter, and pH responsive. (FIGS. 12A-D). Both crosslinked and non-crosslinked particles exhibited a drop in hydrodynamic radius as pH was reduced from 7.4 to 5.8, corresponding to particle disassembly, release of encapsulated cargo, and transition to a membrane destabilizing state (FIGS. 8B-C). Crosslinking was found to increase the effective average molecular weight of polymer chains (FIG. 8A). Crosslinking appears to have a minimal effect on particle diameter at physiological pH (FIGS. 8B-C), indicating that particle cross bridging events are unlikely during the PDSMA reduction process. The degree of crosslinking can be controlled through the molar equivalents of DTT added, which was found to correlated with the degree of membrane destabilization at pH values associated with endosomes and lysosomes (pH 6.6-5.8) in an erythrocyte lysis (hemolysis) assay (FIG. 4). Maximum hemolytic activity was observed when 0.5 molar equivalents of DTT was added, corresponding to the maximum degree of crosslinking achievable using this crosslinking strategy. Optimally crosslinked particles more efficiently caused pH-dependent membrane destabilization than did uncrosslinked particle controls.

Additionally, the vesicles enhance CDN cellular uptake relative to free CDN and respond to endolysosomal acidification by disassembling and intracellularly releasing the CDN payload. Collectively, these data suggest that the described vesicles enhance cGAMP potency by mediating intracellular release of the cGAMP compound and disrupting the endosomal membrane to enhance cytosolic localization of the payload.

Therapeutic Activity of PEG-EBP Polymeric Vesicles for Cancer Treatment

Figure 9A:
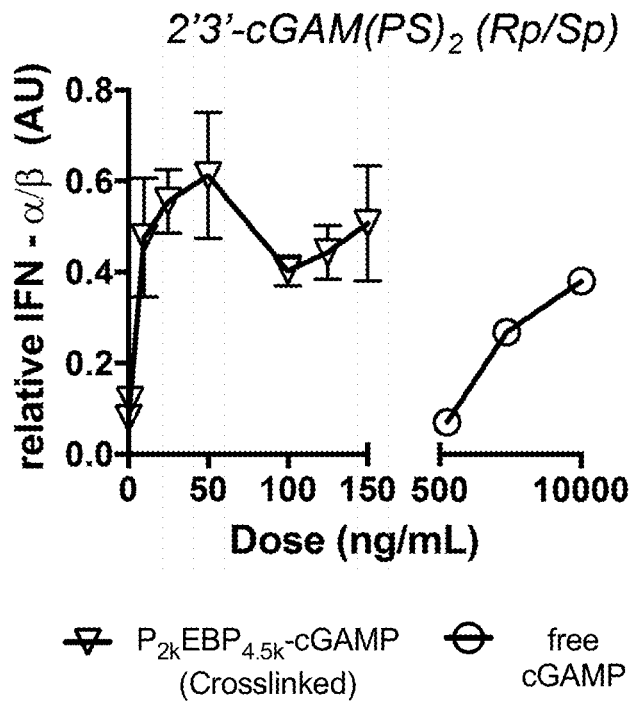
FIGS. 9A-B show graphs illustrating enhanced in vitro potency of cGAMP derivatives (A) 2'3'-cGAM(PS)$_2$ (Rp/Sp) and (B) c-[2'FdGMP]-[2'FdAMP] (both CDNs purchased from Invivogen) when encapsulated in crosslinked PEG-EBP polymer vesicles. Relative levels of type I interferon production were determined using THP1-Blue ISG cells with an interferon regulatory factor inducible secreted embryonic alkaline phosphatase reporter construct.
Figure 9B:
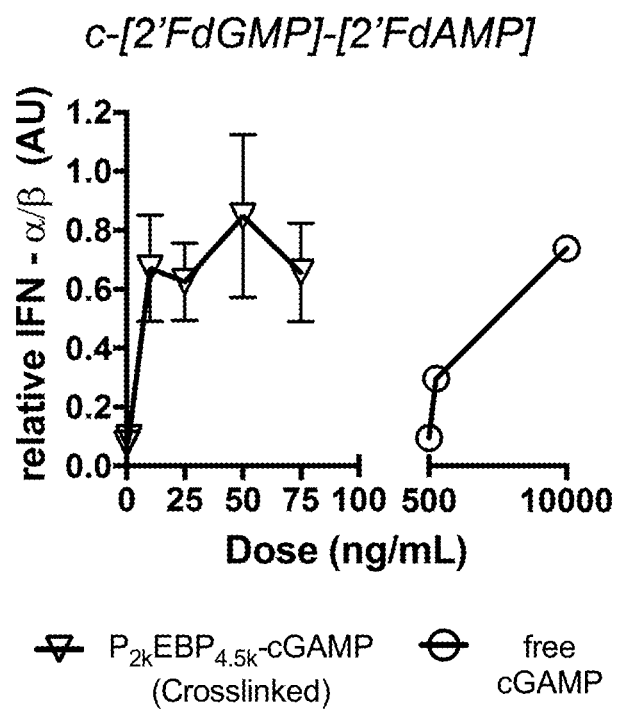
Figure 10A:
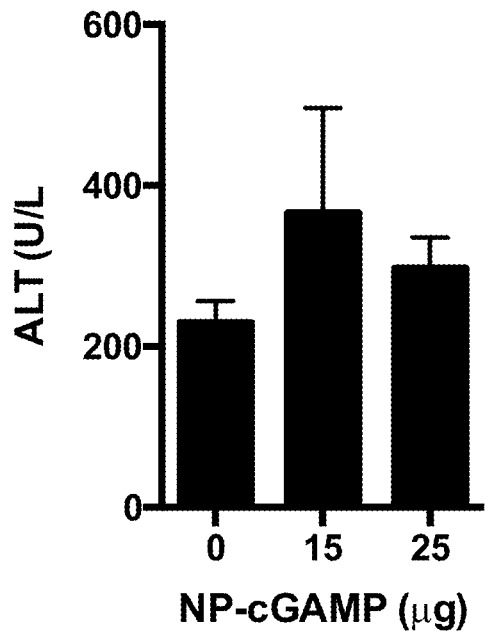
FIGS. 10A-D show graphs demonstrating normal levels of (A) ALT, (B) AST, (C) bilirubin, and (D) creatinine in mouse serum 24 hr after intravenous (tail vein) administration of cGAMP encapsulated in crosslinked PEG-EBP vesicles (NP-cGAMP) at doses corresponding to 15 or 25 µg cGAMP. The zero (0) µg dose corresponds to PBS (vehicle) only.
Figure 10B:
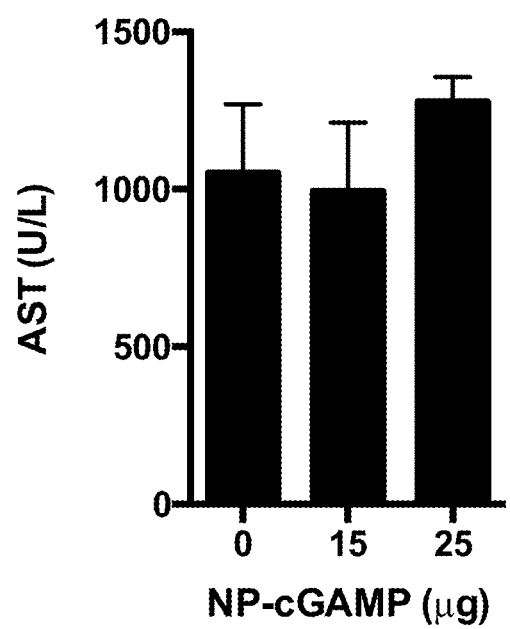
Figure 10C:
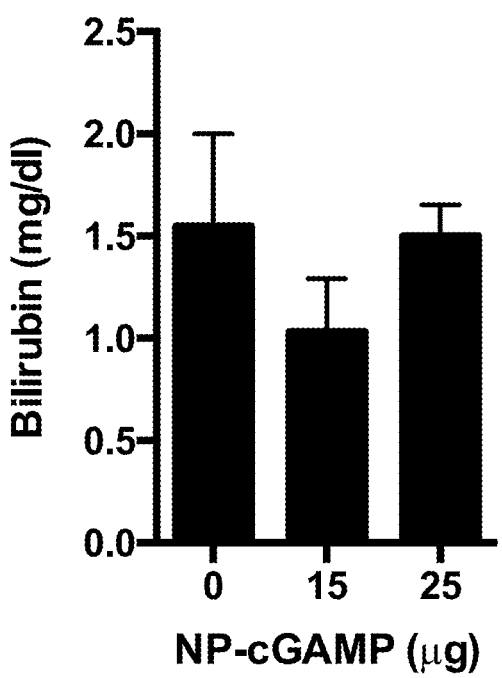
Figure 10D:
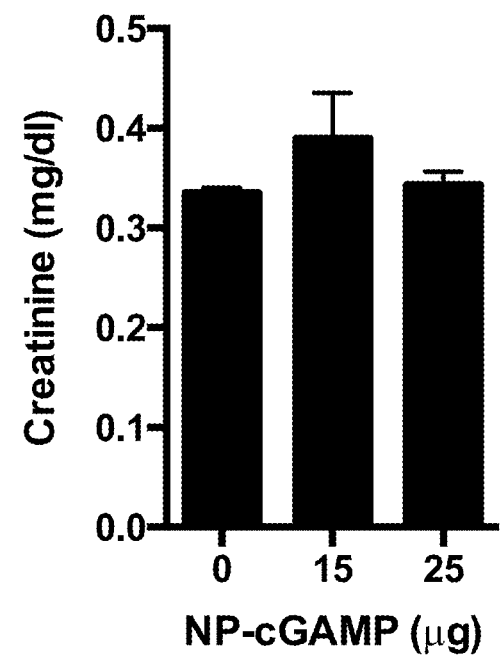

In vitro testing of PEG-EBP encapsulated cGAMP in human monocytic and murine dendritic cell lines both reveals that 24 hr treatments with encapsulated cGAMP results in significantly greater magnitudes of type I interferon production than treatment with equivalent doses of free cGAMP or cGAMP encapsulated within particles exhibiting weaker membrane destabilizing activity (FIGS. 6A-C). Specifically, treatment of human monocytes and murine macrophages and dendritic cells with PEG-EBP encapsulated cGAMP generated a type I interferon response equivalent to that of cells treated with a 1000× greater concentration of free cGAMP (10 ng/mL vs 10000 ng/mL). Trends were qualitatively consistent in both murine and human cell lines. Similar enhancements in activity were observed when the CDNs 2'3'-cGAM(PS)2 (Rp/Sp) and c-[2'FdGMP]-[2'FdAMP] were encapsulated into crosslinked PEG-EBP polymer vesicles (FIGS. 9A-B).

Figure 13A:
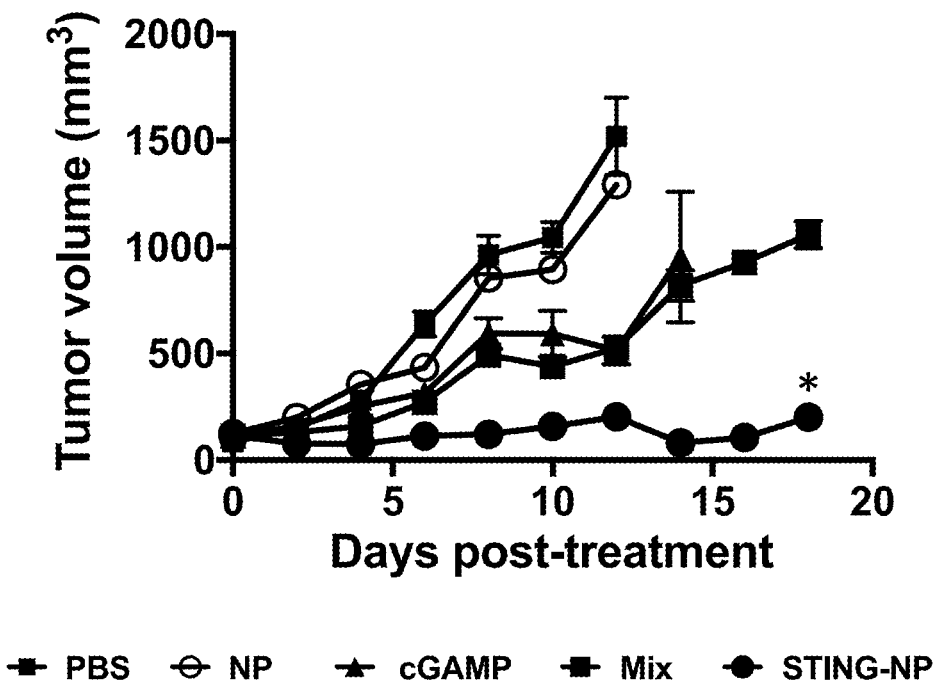
FIGS. 13A-D show graphs illustrating enhanced in vivo potency of cGAMP encapsulated into optimally crosslinked PEG-EBP polymer vesicles. (A) Tumor volume and (B) mouse survival (<1500 mm$^3$ tumor volume) after treatment of subcutaneously established flank B16.F10 melanoma tumors. Mice received intratumoral injections of indicated formulations three times, four days apart following establishment of tumors having an average volume of 100 mm$^3$. NP=empty polymer vesicle; cGAMP=free cGAMP; Mix=physical mixture of empty vesicles and soluble cGAMP; STING-NP=cGAMP encapsulated in crosslinked PEG-EBP polymer vesicles. Doses were normalized based on 10 µg cGAMP per injection. (C-D) show data illustrating ability of cGAMP containing polymer vesicle formulations to generate immunological memory that can prevent tumor growth in response to re-challenge. Mice in studies described in FIG. 9A-B that demonstrated a complete response to therapy (~35% of mice) were re-challenged on day 65 with B16.F10 melanoma cells in the contralateral flank, and tumor volume (C) and survival rates (D) were determined relative to untreated mice that did not previously have tumors.
Figure 13B:
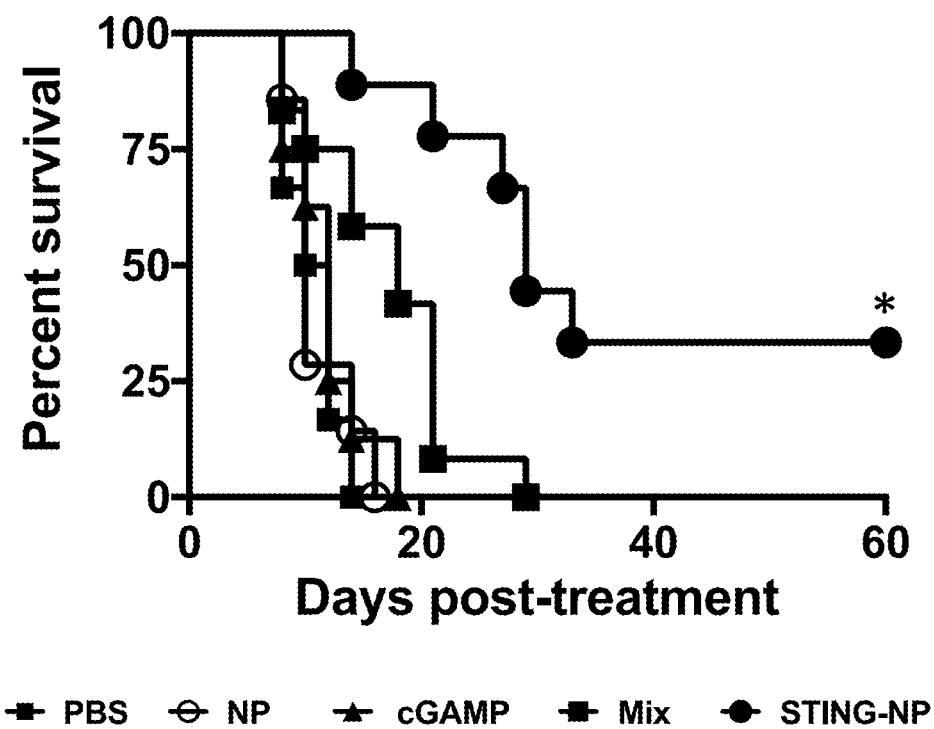
Figure 13C:
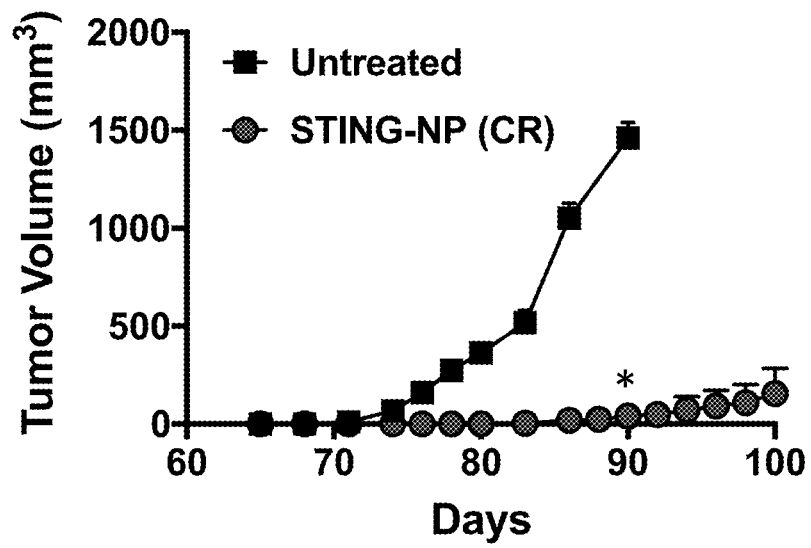
Figure 13D:
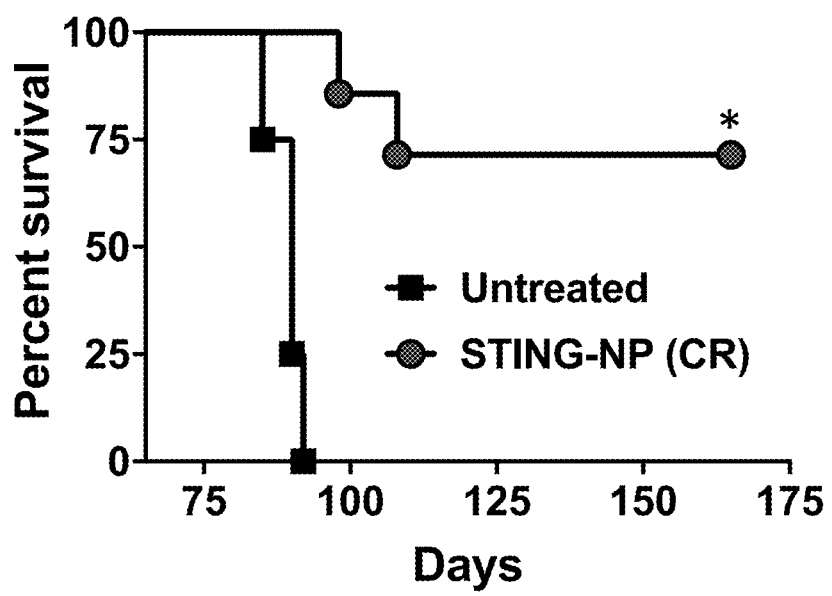

PEG-EBP encapsulated cGAMP formulations were tested in vivo for therapeutic efficacy in a murine melanoma model. Specifically, $5 \times 10^4$ B16F10 melanoma cells were subcutaneously established in the flanks of C57BL6J mice. Upon detection of an average tumor volume of 100 mm$^3$, mice were injected intratumorally with 100 μL of phosphate buffered saline (PBS) containing 10 μg of cGAMP in free, PEG-EBP encapsulated, and physically mixed with PEG-EBP formulations, with two additional injections every 4 days following. Control groups with injections of either PBS or vesicles only were included. Results indicate that treatment with PEG-EBP encapsulated cGAMP yields significant therapeutic benefit, manifesting in slower tumor growth, improved average mouse survival times, and/or an increased incidence of complete responses relative to those of all other test groups (FIGS. 13A-B). Additionally, complete responders were re-challenged with $5 \times 10^4$ B16F10 melanoma cells on the contralateral flank 65 days after initial treatment, with 70% of mice completely rejecting tumors and experiencing long-term survival (FIGS. 13C-D).

Figure 14A:
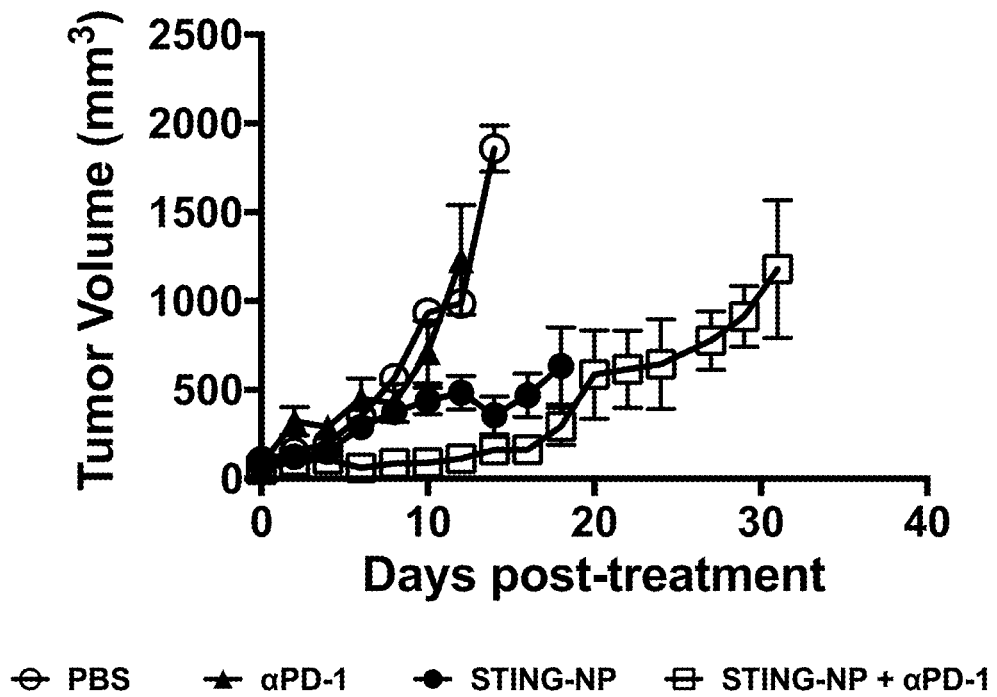
FIGS. 14A-B show graphs illustrating the therapeutic efficacy of cGAMP encapsulated into optimally crosslinked PEG-EBP polymer vesicles in a murine model of neuroblastoma. (A) Tumor volume and (B) mouse survival (<1500 mm$^3$ tumor volume) after treatment of subcutaneously established flank 9464D neuroblastoma tumors. Mice received intratumoral injections of cGAMP encapsulated in crosslinked PEG-EBP polymer vesicles (STING-NP) alone or in combination with i.p. injection of anti-PD-1 (αPD-1) antibody (100 µg) indicated formulations three times, four days apart following establishment of tumors having an average volume of 100 mm$^3$. PBS and αPD-1 antibody alone were administered as controls. Doses were normalized to 10 µg cGAMP per injection.
Figure 14B:
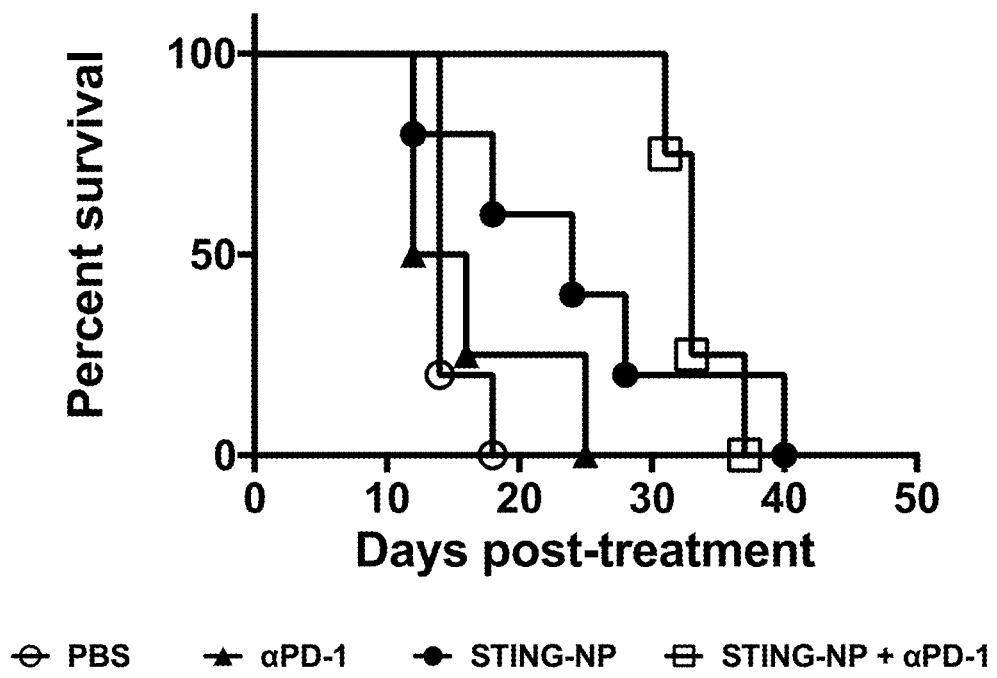

Similar results were observed when evaluated in a murine model of neuroblastoma. Specifically, $1 \times 10^6$ 9464D neuroblastoma cells were subcutaneously established in the flanks of C57BL6J mice. Upon detection of an average tumor volume of 100 mm$^3$, mice were injected intratumorally with 100 μL of phosphate buffered saline (PBS) containing 10 μg of cGAMP encapsulated in PEG-EBP vesicles with two additional injections every 4 days following. In some groups, this treatment was combined with 100 μg of anti-PD-1 antibody injected intraperitoneally. Control groups included injection of PBS or anti-PD-1 antibody alone. Administration of cGAMP in PEG-EBP vesicles slowed tumor growth, extended survival time, and improved the efficacy of anti-PD-1 checkpoint blockade (FIGS. 14A-B). Collectively, these data indicate that PEG-EBP polymeric enhance cGAMP potency both in vitro and in vivo.

Example 2

This example describes polymeric vesicles that actively enhance endosomal escape of encapsulated protein and peptide antigens and CDNs to cytosolic antigen processing and immune surveillance pathways. By including proteins and/or peptides into the aqueous solution during vesicle formation, protein and/or peptide antigens can be incorporated into polymer vesicles, with or without CDNs. A protein antigen, ovalbumin, and a peptide antigen, QLESIINFEKL, were shown to be encapsulated into polymer vesicles assembled using PEG-b-EBP block copolymers with encapsulation efficiencies exceeding 25%. By mixing antigen and CDNs together in aqueous solution during vesicle formation, antigens and CDNs, including but not limited to c-di-GMP and cGAMP, can be co-loaded into polymer vesicles with an average diameter <100 nm and neutral surface charge. Pyridyl disulfide (PDS) moieties were exploited for post-assembly in situ crosslinking of the vesicle membrane via partial reduction of disulfide bonds with DTT.

Formulated PEG-EBP vesicles were screened for their abilities to mediate endosomal leakage using an erythrocyte lysis assay as a model for membrane disruption. Data show optimal particle mediated erythrocyte lysis at 0.5 equivalents of DTT addition, corresponding to a maximum in crosslink density per chain (FIG. 4). A significant dependence of particle mediated hemolysis on chain crosslinking was observed, with up to a five-fold improvement in membrane disruptive capabilities of optimally formulated particles in comparison to uncrosslinked analogues.

Similarly, in situ crosslinking was also shown to significantly improve cytosolic delivery of CDNs to the cytosolic stimulator of interferon genes (STING) in human monocyte cell line (THP-1) and murine macrophage (RAW264.7) and dendritic cell (DC2.4) lines (FIGS. 6A-C and 9A-B).

The optimized particles were then formulated to encapsulate protein and/or peptide antigens and/or CDNs and tested for their abilities to increase STING-dependent type I interferon production by human and murine myeloid cells and/or mediate cross presentation antigen in the DC 2.4 murine dendritic cell line. Antigen mediated cross presentation was quantified via a B3Z reporter T-cell hybridoma or an antibody that recognizes the SIINFEKL epitope in complex with H-2K$^b$ (SIINFEKL-H-2K$^b$).

Figure 15A:
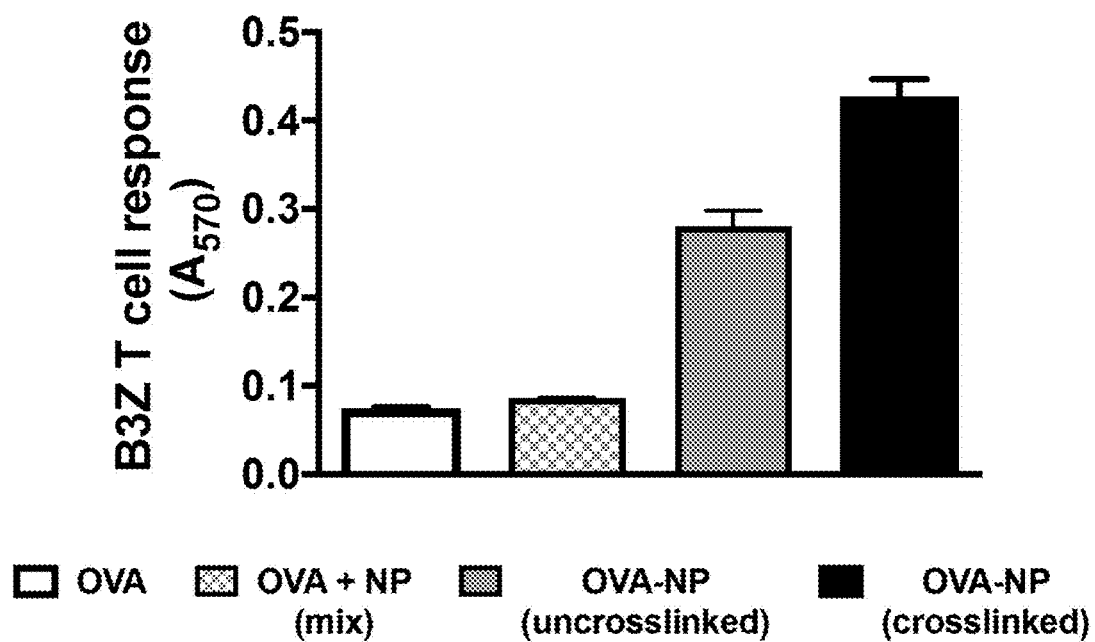
FIGS. 15A-B show graphs illustrating the ability of PEG-EBP polymer vesicles to increase antigen delivery and major histocompatibility complex class I (MHC-I) presentation by murine dendritic cells (DC2.4 cell line). (A) The protein antigen, ovalbumin (OVA), was encapsulated in PEG-EBP polymer vesicles with (OVA-NP(crosslinked)) or without in situ crosslinking (OVA-NP(uncrosslinked) and relative degree of MHC-I antigen presentation by DC2.4 cells assessed using a B3Z-LacZ T cell hybridoma co-culture assay. Free ova (OVA) and a physical mixture of OVA and polymer vesicles (OVA+NP) were run as controls. (B) A model synthetic long peptide (SLP) antigen (QLESIIN-FEKL) was encapsulated in crosslinked PEG-EBP (NP-SLP) with or without cGAMP (NP-cGAMP-SLP) and relative degree of MHC-I antigen presentation by DC2.4 cells assessed using an antibody that recognizes the SIINFEKL epitope in complex with the MHC-I molecule H-2K$^b$ (SI-INFEKL-H-2K$^b$). Free SLP and a physical mixture of SLP and cGAMP were run as controls.
Figure 15B:
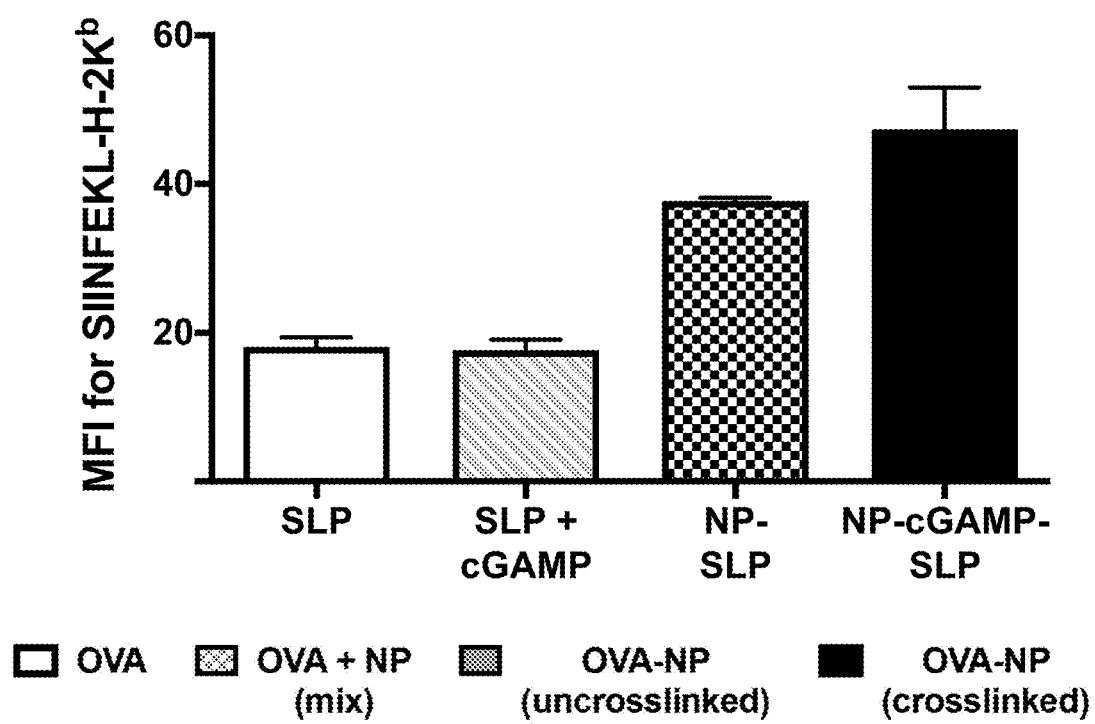
Figure 16A:
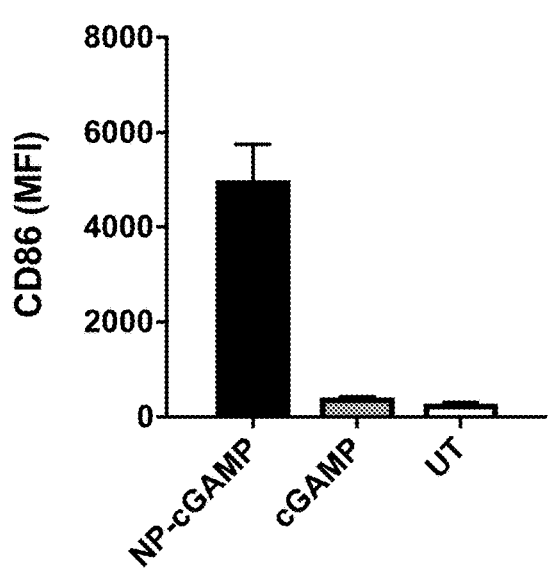
FIGS. 16A-D show graphs illustrating the ability of PEG-EBP polymer vesicles to enhance the immunostimulatory activity of cGAMP in murine bone marrow derived dendritic cells (BMDCs) as indicated by increased cell surface expression of (A) CD86, (B) MHC-I, (C) MHC-II, and (D) CD80 when cGAMP is encapsulated in vesicles (NP-cGAMP) relative to incubation with free cGAMP. UT=untreated.
Figure 16B:
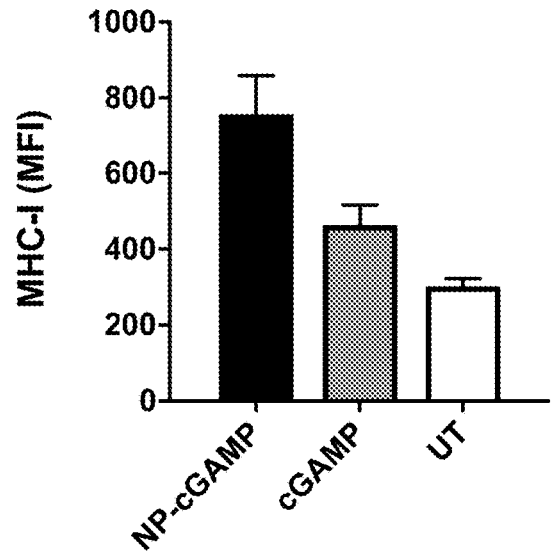
Figure 16C:
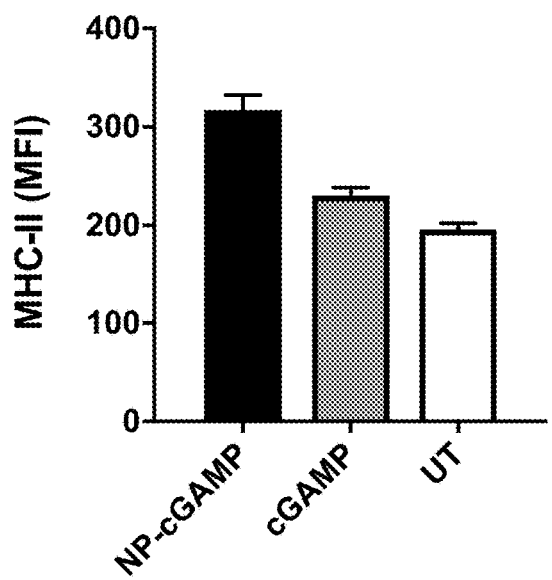
Figure 16D:
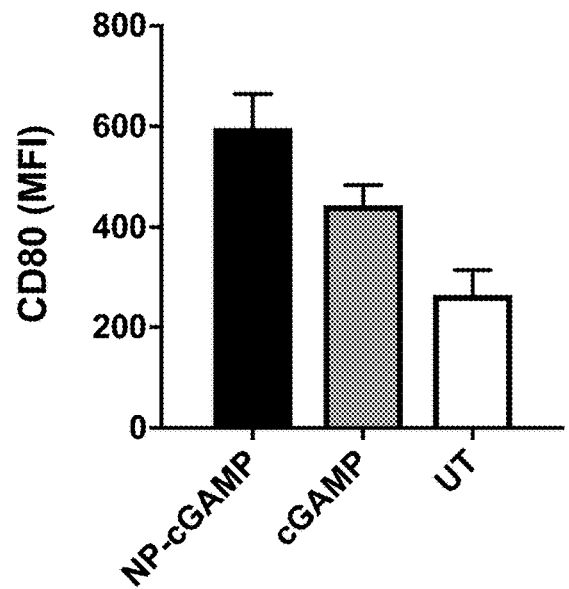

Encapsulation of ovalbumin in the polymer vesicles was shown to increase cross presentation of ovalbumin on major histocompatibility complex class (MHC-I) in murine dendritic cells, with crosslinked particles promoting significantly higher class I presentation relative to the uncrosslinked variant or a physical mixture of vesicles and soluble ovalbumin (FIG. 15A). Encapsulation of peptide antigens in the polymer vesicles was also shown to increase antigen presentation on MHC-I, with dual-delivery of peptide antigens and CDNs in the polymer vesicles further enhancing presentation (FIG. 15B). Additionally, co-encapsulation of cGAMP and peptide antigen in polymer vesicles increased MHC-I antigen presentation relative to vesicles containing peptide only or a physical mixture of soluble cGAMP and peptide. Encapsulated cGAMP was also shown to enhance bone marrow derived dendritic cell (BMDC) activation in vitro as indicated by increased expression of MHC-II, MHC-I, CD86, and CD80 relative to free cGAMP (FIGS. 16A-D). Collectively, these data demonstrate that endosomolytic polymer nanoparticles provide a versatile vaccine delivery platform for targeting cytosolic immunoregulatory machinery.

Figure 17A:
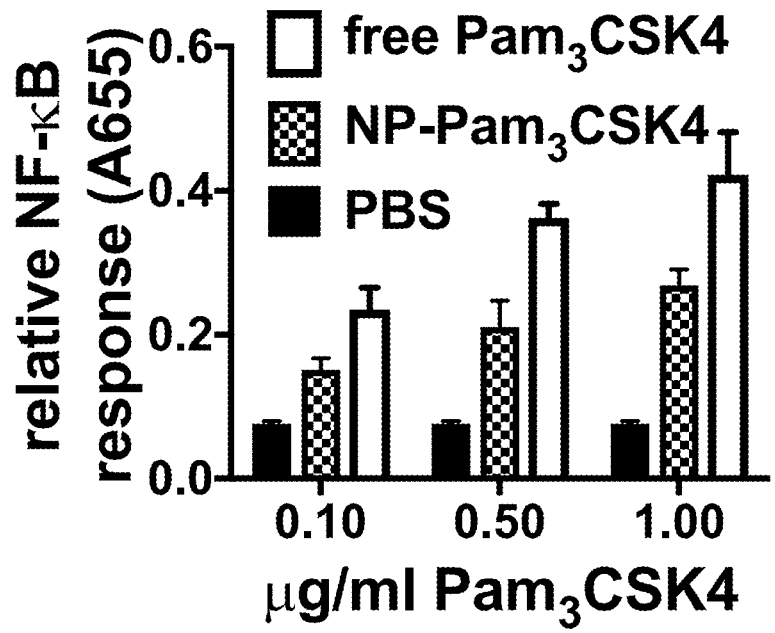
FIGS. 17A-B show graphs illustrating the ability of PEG-EBP polymer vesicles to deliver immunostimulatory cargo that activate receptors on the cell surface or within endosomal compartments. (A) Shows the amphiphilic TLR-2 ligand Pam$_3$CSK4 incorporated into the membrane of PEG-EBP vesicles (NP-Pam$_3$CSK4) compared to PBS only and free Pam$_3$CSK4. (B) Shows the endosomal TLR-9 agonist CpG ODN 1826 encapsulated into PEG-EBP vesicles (NP-CpG) with and without crosslinking, as compared to PBS and free CpG.

PEG-EBP polymer vesicles were also shown to serve as a carrier for agonists of pattern recognition receptors (PRRs) that reside on the cell surface. As illustrated in FIG. 17A, immunostimulatory activity is partially retained, as determined in a RAW264.7 NF-κB reported cell assay, when the amphiphilic toll-like receptor (TLR)-2 ligand Pam$_3$CSK4 is incorporated into the vesicle membrane. The reduced activity of Pam$_3$CSK4 incorporated into vesicles is thought to be primarily related to the ~50% of Pam$_3$CSK4 molecules that are incorporated into the inner leaflet of the vesicle membrane, and therefore are not accessible for binding to cell surface TLR-2 molecules. Combined with data demonstrating the ability of PEG-EBP polymer vesicles to enhance CDN delivery, these data support the use of polymer vesicles for delivery of adjuvant combinations that include CDNs and agonists of cell surface pattern recognition receptors (e.g., TLR-2, TLR-4).

Figure 17B:
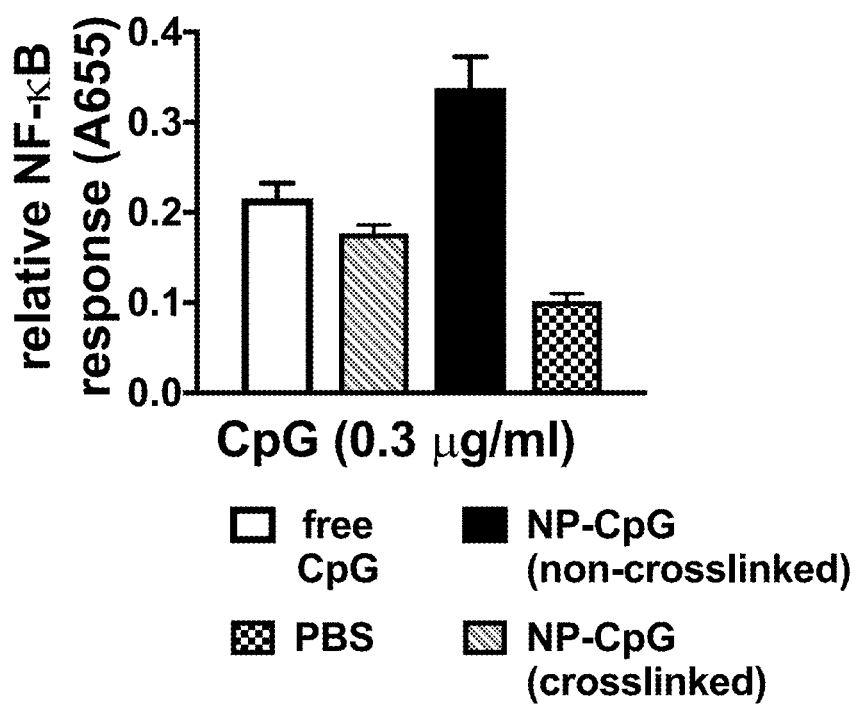

PEG-EBP polymer vesicles were further shown to serve as a carrier for agonists of pattern recognition receptors (PRRs) that reside within endosomal compartments. As illustrated in FIG. 17B, when the oligonucleotide and TLR-9 ligand CpG ODN1826 (CpG) is incorporated into the vesicle, the extent of vesicle crosslinking modulates the immunostimulatory activity of CpG. CpG activity is enhanced relative to soluble control (free CpG) in non-crosslinked vesicles, likely owing to increased cellular uptake and release within endosomal compartments where TLR-9 is localized. The activity of CpG in crosslinked vesicles is comparable to free CpG, potentially reflecting the increased percentage of CpG that escapes to the cytosol due to crosslinking and is therefore not endosomally localized. These data support the ability to regulate CpG-dependent TLR-9 activation through control of vesicle crosslinking and/or membrane destabilizing potency. This data also supports the use of polymer vesicles for delivery of adjuvant combinations that include CDNs and agonists of endosomal pattern recognition receptors (e.g., TLR-9, TLR-7, TLR-8).

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A diblock copolymer, comprising:
   a hydrophilic first block; and
   a terpolymer second block including:
      amine containing monomers;
      hydrophobic monomers; and
      crosslinkable monomers selected from the group consisting of pyridyl disulfide monomers, azide-functionalized monomers, thiol-functionalized monomers, amine-functionalized monomers, photocrosslinkable monomers, and combinations thereof.

2. The diblock copolymer of claim 1, wherein the hydrophilic block is between about 25% and about 35% of the total mass of the diblock copolymer.

3. The diblock copolymer of claim 1, wherein the hydrophilic block is selected from the group consisting of polyethers, polyesters, polycarbonates, polyvinyls, polyamino acids, polysulfobetaines, carboxybetaines, and combinations thereof.

4. The diblock copolymer of claim 3, wherein the hydrophilic block is polyethylene glycol (PEG).

5. The diblock copolymer of claim 1, wherein the hydrophilic block has a molecular weight of between about 1 kDa and about 3 kDa.

6. The diblock copolymer of claim 1, wherein the mole percent of the amine containing monomers in the second block is between 40% and 70%.

7. The diblock copolymer of claim 1, wherein the mole percent of the hydrophobic monomers in the second block is between 30% and 60%.

8. The diblock copolymer of claim 1, wherein the mole percent of the crosslinkable monomers in the second block is between 2% and 16%.

9. The diblock copolymer of claim 1, wherein the amine containing monomers are selected from the group consisting of (2-diethylamino) ethyl methacrylate (DEAEMA), 2-(dimethylamino)ethyl methacrylate, 2-(diisopropylamino)ethyl methacrylate, 2-N-morpholinoethyl methacrylate, 2-amino methacrylate hydrochloride, and combinations thereof.

10. The diblock copolymer of claim 1, wherein the hydrophobic monomers are selected from the group consisting of acrylates, alkyl methacrylates, methacrylates with fluorinated or aromatic pendant groups, and combinations thereof.

11. The diblock copolymer of claim 10, wherein the alkyl methacrylates are selected from the group consisting of butyl methacrylate (BMA), hexyl methacrylate, octyl methacrylate, decyl methacrylate, and/or lauryl methacrylate.

12. The diblock copolymer of claim 1, wherein the second block has a molecular weight of between 3 kDa and 6 kDa.

13. The diblock copolymer of claim 1, wherein the copolymer comprises the formula:

[polyethylene glycol]$_m$-b-[((2-diethylamino) ethyl methacrylate)$_x$-c-(butyl methacrylate)$_y$-c-(pyridyl disulfide ethyl methacrylate)$_z$]$_n$;

wherein m is between 1 and 3 kDa;
wherein n is between 3 and 6 kDa;
wherein x is between 40 and 70 mole percent;
wherein y is between 30 and 60 mole percent; and
wherein z is between 0 and 16 mole percent.

14. The diblock copolymer of claim 13, wherein m is 2 kDa and n is 4.5 kDa.

15. The diblock copolymer of claim 13, wherein x is 57 mole percent, y is 35 mole percent, and z is 8 mole percent.

16. The diblock copolymer of claim 1, wherein the copolymer is crosslinked through the crosslinkable monomers.

17. The diblock copolymer of claim 1, wherein the copolymer is self-assembling.

18. A polymer vesicle, comprising:
   a diblock copolymer including:
      a hydrophilic first block; and
      a terpolymer second block including:
         amine containing monomers;
         hydrophobic monomers; and
         crosslinkable monomers selected from the group consisting of pyridyl disulfide monomers, azide-functionalized monomers, thiol-functionalized monomers, amine-functionalized monomers, photocrosslinkable monomers, and combinations thereof; and
   at least one active agent loaded in the polymer vesicle;
   wherein the second block forms an inner hydrophobic domain of a vesicle membrane and the hydrophilic block forms a corona facing the exterior and aqueous interior of the vesicle membrane, the corona providing an outer shell that stabilizes the vesicle in aqueous media.

19. The polymer vesicle of claim 18, wherein the diblock copolymer comprises the formula:

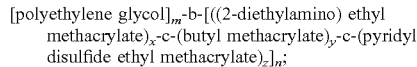

wherein m is between 1 and 3 kDa;
wherein n is between 3 and 6 kDa;
wherein x is between 40 and 70 mole percent;
wherein y is between 30 and 60 mole percent; and
wherein z is between 2 and 16 mole percent.

20. The polymer vesicle of claim 19, wherein m is 2 kDa and n is 4.5 kDa.

21. The polymer vesicle of claim 19, wherein x is 57 mole percent, y is 35 mole percent, and z is 8 mole percent.

22. The polymer vesicle of claim 18, wherein the vesicle is pH-responsive.

23. The polymer vesicle of claim 22, wherein the vesicle is stable at physiological pH, and is disassembled at a pH of about 6.5.

24. The polymer vesicle of claim 18, wherein the vesicle is crosslinked through the crosslinkable monomers.

25. The polymer vesicle of claim 18, wherein the active agent is a stimulator of interferon genes (STING) agonist.

26. The polymer vesicle of claim 25, wherein the STING agonist is released by the vesicle at a pH of about 6.5.

27. The polymer vesicle of claim 18, wherein the active agent is a cyclic dinucleotide (CDN).

28. A method of forming a polymer vesicle, the method comprising:
synthesizing the diblock copolymer of claim 1 through a polymerization technique selected from the group consisting of addition polymerization, condensation polymerization, and a combination thereof;
providing at least one active agent; and
assembling the polymer vesicle.

29. The method of claim 28, wherein the active agent is a stimulator of interferon genes (STING) agonist or antagonist.

30. The method of claim 28, wherein the active agent is a cyclic dinucleotide (CDN).

31. The method of claim 28, wherein the active agent comprises at least one antigen and at least one cyclic dinucleotide (CDN).

32. A method of administering an active agent to a cell, the method comprising:
administering a polymer vesicle loaded with the active agent to the cell, the polymer vesicle comprising a diblock copolymer including:
a hydrophilic first block; and
a terpolymer second block including:
amine containing monomers;
hydrophobic monomers; and
crosslinkable monomers selected from the group consisting of pyridyl disulfide monomers, azide-functionalized monomers, thiol-functionalized monomers, amine-functionalized monomers, photocrosslinkable monomers, and combinations thereof;
wherein the second block forms an inner hydrophobic domain of a vesicle membrane and the hydrophilic first block forms a corona facing the exterior and aqueous interior of the vesicle membrane, the corona providing an outer shell that stabilizes the vesicle in aqueous media; and
wherein the polymer vesicle enters an endosomal location within the cell and is destabilized at endosomal pH, thereby releasing the active agent within the cell.

33. The method of claim 32, wherein the diblock copolymer comprises the formula:

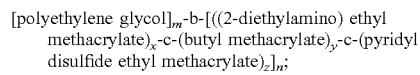

wherein m is between 1 and 3 kDa;
wherein n is between 3 and 6 kDa;
wherein x is between 40 and 70 mole percent;
wherein y is between 30 and 60 mole percent; and
wherein z is between 2 and 16 mole percent.

34. The method of claim 33, wherein m is 2 kDa and n is 4.5 kDa.

35. The method of claim 34, wherein x is 57 mole percent, y is 35 mole percent, and z is 8 mole percent.

36. The method of claim 32, wherein the vesicle is stable at physiological pH, and is disassembled at a pH of about 6.5.

37. The method of claim 32, wherein the vesicle is crosslinked through the crosslinkable monomers.

38. The method of claim 32, wherein the active agent is a stimulator of interferon genes (STING) agonist.

39. The method of claim 38, wherein the active agent is a cyclic dinucleotide (CDN).

40. The method of claim 32, wherein the polymer vesicle is administered to an organism.

41. The method of claim 40, wherein the organism is a human.

42. The method of claim 40, wherein the administration is by a route selected from the group consisting of intratumoral injection, intravenous (IV), subcutaneous, or a combination thereof. Other routes of administration may include oral, topical, cutaneous, transdermal, intradermal, intramuscular, intraperitoneal, intracranial, mucosal, transmucosal, intranasal, pulmonary, inhalation, direct intraventricular, rectal, intestinal, parenteral, intramedullary, intrathecal, intraocular, insufflation, intra-arterial, and combinations thereof.

43. The method of claim 32, wherein the cell is a cancer cell.

* * * * *